(12) United States Patent
Prentice et al.

(10) Patent No.: US 9,187,766 B2
(45) Date of Patent: Nov. 17, 2015

(54) ACCUMULATION OF METABOLIC PRODUCTS IN BACTERIAL MICROCOMPARTMENTS

(71) Applicants: University College Cork National University of Ireland, Cork (IE); University of Kent, Canterbury Kent (GB)

(72) Inventors: Michael Prentice, Cork (IE); Martin Warren, Canterbury Kent (IE); Mingzhi Liang, Cork (IE)

(73) Assignees: University College Cork, National University of Ireland, Cork (IE); University of Kent, Canterbury Kent (GB)

( * ) Notice: Subject to any disclaimer, the term of this patent is extended or adjusted under 35 U.S.C. 154(b) by 38 days.

(21) Appl. No.: 14/347,527

(22) PCT Filed: Sep. 27, 2012

(86) PCT No.: PCT/EP2012/069106
§ 371 (c)(1),
(2) Date: Mar. 26, 2014

(87) PCT Pub. No.: WO2013/045562
PCT Pub. Date: Apr. 4, 2013

(65) Prior Publication Data
US 2014/0328801 A1 Nov. 6, 2014

(30) Foreign Application Priority Data

Sep. 28, 2011 (EP) .................................. 11183154

(51) Int. Cl.
| | |
|---|---|
| *C07K 14/19* | (2006.01) |
| *C12Q 1/02* | (2006.01) |
| *C12P 3/00* | (2006.01) |
| *A23L 1/30* | (2006.01) |
| *C07K 14/195* | (2006.01) |
| *C12N 1/20* | (2006.01) |
| *C12N 9/12* | (2006.01) |
| *C12N 15/70* | (2006.01) |
| *C12P 21/00* | (2006.01) |
| *A61K 38/45* | (2006.01) |

(52) U.S. Cl.
CPC .................. *C12P 3/00* (2013.01); *A23L 1/3014* (2013.01); *C07K 14/195* (2013.01); *C12N 1/20* (2013.01); *C12N 9/1229* (2013.01); *C12N 15/70* (2013.01); *C12P 21/00* (2013.01); *C12Y 207/04001* (2013.01); *A61K 38/45* (2013.01)

(58) Field of Classification Search
CPC ..... C07K 14/195; C07K 2319/01; C12Q 1/02
See application file for complete search history.

(56) References Cited

U.S. PATENT DOCUMENTS

2014/0295520 A1* 10/2014 Schmidt-Dannert et al. . 435/170

FOREIGN PATENT DOCUMENTS

| WO | WO-2011/017458 | 2/2011 |
|---|---|---|
| WO | WO-2011/094765 | 8/2011 |

OTHER PUBLICATIONS

Choudhary et al. 2012; Engineered protein nano-compartments for targeting enzyme localization. PLOS one 7(3): e33342.*
Parsons et al. 2008; Biochemical and structural insights into bacterial organelle form and biogenesis. J. Biol. Chem. 283(21): 14366-143750.*
Parsons et al. 2010; Synthesis of empty bacterial microcompartments, directed organelle protein incorporation, and evidence of filament-associated organelle movement. Molecular Cell. 38: 205-315.*
Fan et al. 2010; Short N-terminal sequences package proteins into bacterial microcompartments. PNAS. 107(16): 7509-7514.*
Parsons, et al. "Synthesis of Empty Bacterial Microcompartments, Directed Orangelle Protein Incorporation, and Evidence of Filament-Associated Organelle Movement", Molecular Cell, vol. 38, No. 2, Apr. 2010.
Liberton, et al., "Unique Thylakoid Membrane Architecture of Unicellular N2-Fixing Cyanobaterium Revealed by Electron Tomography". Plant Physiology, vol. 155, No, 4, Apr. 2011.
Hong, et al., "Pattern of cyanophycin accumulation in nitrogen-fixing and non-nitrogen-fixing cyanobacteria", Archives of Microbiology, vol. 176, No. 1-2, Jul. 2001.

(Continued)

*Primary Examiner* — Karen Cochrane Carlson
(74) *Attorney, Agent, or Firm* — Cesari and McKenna, LLP

(57) ABSTRACT

A non-therapeutic method of accumulating a polymeric or high molecular weight molecular product within a bacterial microcompartment in bacterial cytoplasm, which method employs a recombinant bacteria which is transformed to express a microcompartment containing an enzyme capable of converting a low molecular weight substrate into a polymeric or high molecular weight product, the method comprising the steps of: incubating the recombinant bacteria with the low-molecular weight substrate, or a precursor of the low molecular weight substrate which is capable of being metabolized to the substrate within the recombinant bacteria, such that the substrate or precursor is taken up by the bacteria, wherein the substrate enters the microcompartment and the enzyme within the microcompartment converts the substrate to a polymeric or high molecular weight molecular product, and wherein the polymeric or high molecular weight molecular product is accumulated within the microcompartment due to its size.

17 Claims, 6 Drawing Sheets

(56) References Cited

OTHER PUBLICATIONS

McGrath, et al., "Microbial phosphate removal and polyphosphate production from wastewaters", Advances in Applied Microbiology, Academic Press, vol. 52, Jan. 2003.

Kato, et al., "Genetic improvement of *Escherichia coli* for enhanced biological removal of phosphate from wastewater.", Applied and Environmental Microbiology, vol. 59, No. 11, Nov. 1993.

Seufferheld, et al., "Identification of Organelles in Bacteria Similar to Acidocalcisomes of Unicellular Eukaryotes", Journal of Biological Chemistry, vol. 278, No. 32, Aug. 2003.

Docampo, et al., "Acidocalcisomes", Cell Calcium, vol. 50, No. 2, Aug. 2011.

Parsons, et al., "Biochemical and Structural Insights into Bacterial Organelle Form and Biogenesis", Journal of Biological Chemistry, vol. 283, No. 21, May 2008.

* cited by examiner

ACCUMULATION OF METABOLIC PRODUCTS IN BACTERIAL MICROCOMPARTMENTS

CROSS-REFERENCE TO RELATED APPLICATIONS

This application is the National Stage of International Application No. PCT/EP2012/069106, filed on Sep. 27, 2012, which claims the benefit of European Application No. 11183154.1 filed on Sep. 28, 2011. The contents of both applications are hereby incorporated by reference in their entirety.

FIELD OF THE INVENTION

The invention relates to a method for accumulation of compounds inside bacterial cells. In particular, the invention relates to a method for and uses of accumulating compounds within a recombinant bacterial compartment.

BACKGROUND TO THE INVENTION

Bacterial microcompartments (metabolosomes) are closed polyhedral shells 100-150 nm diameter made of thin protein sheets (with pores less than 1 nm in diameter which can be positively or negatively charged), enclosing enzymes and cofactors for carbon fixation (carboxysomes) or various forms of fermentative metabolism. Although bacterial microcompartments were first seen over fifty years ago in photosynthetic cyanobacteria, their presence in the cytoplasm of heterotrophic bacteria was only confirmed in 1998, because they require induction by specific metabolites to form. In fact, twenty percent of bacterial genome sequences contain microcompartment structural genes, in many cases associated with enzymes of unknown function. A high percentage of bacteria therefore make a major investment in retaining and expressing large (20+ gene) operons encoding these structures and associated enzymes. It is believed the structures help bacterial metabolic efficiency by selective limitation of the shell pores on the passage of reactants, by metabolic channeling, or other mechanisms achieving temporary retention of small reaction intermediates within the structure, but these advantages have not been fully quantified.

Native microcompartment operons consist of a combination of genes specifying structural components making up the microcompartment shell, and genes specifying enzymes or cofactors, which are located within the microcompartment, or process products leaving the microcompartment. The diameter of identified pores in microcompartment shells of heterotrophic bacteria is sufficient to admit the typical primary substrates such as 1,2-propanediol, glycerol, or ethanolamine (Table 1). Most molecules consumed or produced by the natural enzyme-catalysed reactions within the microcompartment are less than 100 Daltons. The largest substrate molecules believed to enter and leave native microcompartments (on the basis of the location of the enzyme which utilises them) are cofactors such as Coenzyme A (MW 767.54 Da) which circulate between the microcompartment interior and the cytoplasm. Although they are present in commensal bacteria, expression of different microcompartment operons occurs in enteric pathogens in the intestine and after phagocytosis.

Recombinant microcompartments can be expressed heterologously in *E. coli*, both with and without the associated interior enzyme (Parsons, J., S. Frank, D. Bhella, M. Liang, M. B. Prentice, D. Mulvihill, and M. J. Warren, *Synthesis of Empty Bacterial Microcompartments, Directed Organelle Protein Incorporation, and Evidence of Filament-Associated Organelle Movement*. Molecular Cell, 2010. 38: p. 305-315). A clonable localisation signal comprising a short peptide enabling enzyme targeting to the microcompartment interior has been identified. Fusion of a 42 amino acid peptide (Parsons et al. 2010). or an 18 amino acid peptide (Fan, C., S. Cheng, Y. Liu, C. M. Escobar, C. S. Crowley, R. E. Jefferson, T. O. Yeates, and T. A. Bobik, *Short N-terminal sequences package proteins into bacterial microcompartments*. Proc Natl Acad Sci USA, 2010. 107(16): p. 7509-14) from the N-terminus of PduP enzymes localised green fluorescent protein within microcompartments. Multiple sequence alignment of microcompartment associated enzymes reveals conserved N-terminal extensions of approximately 18 amino acids compared with non-microcompartment associated homologues for diol dehydratase small and medium subunits (PduD,E) ethanolamine ammonia lyase small subunit Eut C, Eut G, and pyruvate formate lyase Pfl2 (Fan et al 2010). General features of these N-terminal extensions, incorporating conserved hydrophobic residues followed by a less conserved linker region have been described (Sutter, M., D. Boehringer, S. Gutmann, S. Gunther, D. Prangishvili, M. J. Loessner, K. O. Stetter, E. Weber-Ban, and N. Ban, *Structural basis of enzyme encapsulation into a bacterial nanocompartment*. Nat Struct Mol Biol, 2008. 15(9): p. 939-947). Compartmentalisation of the cellular interior is a functionally transforming process which underlies such radical events as the emergence of eukaryotes. Nanotechnological applications of biological compartment systems have included the use of viral capsids for DNA delivery and lumazine synthase enclosure of HIV protease (Worsdorfer, B., K. J. Woycechowsky, and D. Hilvert, *Directed evolution of a protein container*. Science, 2011. 331(6017): p. 589-92). Bacteria contain certain polymeric compounds often used as energy or nutrient stores, which are subject to dynamic synthesis and breakdown by different enzymes, according to prevailing conditions, usually under global regulatory control. One example is cyanophycin, an amino acid polymer originally detected in cyanobacteria and formed by the action of cyanophycin synthetase CphA, an enzyme which can be produced in recombinant form in *E. coli* (Aboulmagd, E., F. B. Oppermann-Sanio, and A. Steinbüchel, *Molecular characterization of the cyanophycin synthetase from Synechocystis sp. strain PCC6308*. Archives of Microbiology, 2000. 174(5): p. 297-306.)

Another example, polyphosphate kinase PPK1 (E.C. 2.7.4.1), forms inorganic polyphosphate polymers (metachromatic volutin granules) in bacterial cytoplasm by catalysing the reaction $nATP \leftrightarrow (polyphosphate)_n + nADP$. This enzyme was the first enzyme (PPK) recognised to catalyse polyphosphate synthesis and is now usually termed PPK1 to differentiate it from another subsequently described group of enzymes (PPK2) which primarily catalyse GTP synthesis but also have limited phosphate polymerising capacity. Generally, any mentions of polyphosphate kinase or PPK without qualification in the literature and herein refer to PPK1. PPK1 is widely distributed in bacteria and some eukaryotes and is characterised by a highly conserved ATP-binding tunnel containing an autophosphorylating histidine residue (Zhu, Y., W. Huang, S. S. Lee, and W. Xu, *Crystal structure of a polyphosphate kinase and its implications for polyphosphate synthesis*. EMBO Rep, 2005. 6(7): p. 681-7). Dimerization is crucial for the enzymatic activity of PPK1. A PPK1 monomer includes four structural domains, the N-terminal (N) domain, the head (H) domain, and two related C-terminal (C1 and C2) domains. The ATP-binding tunnel is formed by N, C1, and C2 domains, so conserved residues required for ATP-binding are distributed throughout the length of all known PPK1 proteins. Although nATP←(polyphosphate)$_n$+nADP is a reversible reaction, in *E. coli* this enzyme generally favours synthesis of polyphosphate over breakdown ($V_{max}$ ratio of 4.1). However, the balance between net accumulation and breakdown changes dynamically with growth phase, and external stimuli, in part due to the action of other enzymes.

*E. coli* also contains two exopolyphosphatases which release orthophosphate from the termini of long chain polyphosphate: (polyphosphate)$_n$→(polyphosphate)$_{n-1}$+Pi. These are PPX (E.C. 3.6.1.11, sometimes called PPX1) and its homologue guanosine pentaphosphate phosphohydrolase (GPPA or PPX2), both described by InterPro Accession IPR003695. GPPA (E.C. 3.6.1.40) also hydrolyses guanosine pentaphosphate (pppGpp) to guanosine tetraphosphate (ppGpp) with phosphate release, and pppGpp is a competitive inhibitor of PPX and the polyphosphate hydrolytic activity of GPPA. Amino acid starvation in *E. coli* leads to accumulation of large amounts of polyphosphate due to high levels of pppGpp produced in the stringent response inhibiting PPX.

Phosphate pollution in waterways and water treatment plants is a major problem. Removal of phosphate from wastewater is required to treat agricultural phosphate-containing discharges to reduce eutrophication, the algal blooms and "dead zones" in lakes and coastal marine ecosystems. The established biological method to remove inorganic phosphate from wastewater (Enhanced Biological Phosphate Removal, EBPR) relies on empirical selection by cyclical aerobic and anaerobic incubation of a community of uncultivated bacteria capable of temporary polyphosphate storage. There are various disadvantages to the process: the microbiological basis is not understood, it can take months of pumping to become established, and it is thereafter operationally unstable (prone to unexplained failure).

In medicine, oral phosphorus chelation therapy is required in the management of chronic renal failure subjects because of toxicity resulting from accumulation of dietary phosphate in the absence of urinary secretion (hyperphosphatemia). One method that was used for reducing phosphate in such subjects was the use of oral aluminum hydroxide. However, the use of aluminum hydroxide has severe side-effects due to build up of aluminum in the body. Calcium-based salts are an effective replacement for aluminum therapy and are currently the most widely used but there is a concern about their association with hypercalcaemia and vascular calcification. Newer oral phosphate binding medicaments with fewer side effects have recently been introduced in place of aluminum hydroxide and calcium-based salts, namely the anion exchange resin sevelamer hydrochloride, and lanthanum carbonate. However, these are both much more expensive than calcium or aluminium salts and financial considerations may adversely affect their provision for all renal patients requiring phosphate binding therapy.

It is an object of the present invention to overcome some of the above-mentioned problems.

SUMMARY OF THE INVENTION

The invention provides a means to accumulate polymeric metabolic products or metabolic products of high molecular weight within bacterial microcompartments as set out in the appended claims. The invention employs bacteria that are genetically modified or transformed to express a heterologous bacterial microcompartment, an enzyme that is capable of converting a low molecular weight substrate into a high molecular weight or polymeric product, and a bacterial microcompartment localisation signal that is capable of targeting the enzyme to the microcompartment. Two specific applications of this invention are given as an illustrative example of the utility of the invention. The first application is a method of removing or reducing the levels of inorganic phosphate from a system or environment by employing recombinant bacteria which are capable of non-reversibly accumulating phosphate in the form of the polymer polyphosphate. The second application is a method for accumulating an amino acid polymer (cyanophycin) with an increase in chain length.

In the first example, the bacteria are genetically transformed such that they express microcompartments containing polyphosphate kinase enzyme (ideally PPK1 enzyme), which form a sink for Pi in the system which after normal metabolic uptake by the bacteria is naturally incorporated into the essential coenzyme adenosine triphosphate (ATP) which passes into the microcompartments where it is converted into polyphosphate. As the polyphosphate polymer molecule is too large to pass out of the pores of the microcompartments, it accumulates as a localised phosphate store in the microcompartments. The microcompartment structure generates irreversibility in the process by excluding exopolyphosphatases, and thus preventing phosphate (Pi) liberation from polyphosphate to be lost from the bacterial cell and eventually returned to the system/environment. Data presented below shows that compartmentalisation of PPK1 enzyme has resulted in two-fold uptake and retention of phosphate compared with PPK1 over-expression alone.

In the second example, the bacteria are genetically transformed such that they express microcompartments containing cyanophycin synthetase (CphA), an enzyme capable of assembling a long chain amino acid polymer (cyanophycin). It is well known that expression of cyanobacterial CphA alone in *E. coli* without the cyanobacterial peptidase cyanophycinase (CphB) results in cyanophycin accumulation. Data presented below shows that an increase in chain length of cyanophycin is obtained by localisation of CphA within a microcompartment compared with expression of CphA alone. Thus, a consistent feature of the intracompartment localising process with two different enzyme classes is the enhanced stabilisation of a polymeric molecule.

According to the invention, there is provided a method of accumulating a polymeric or high molecular weight molecular product within a bacterial microcompartment in bacterial cytoplasm, which method employs a recombinant bacteria which is transformed to express a heterologous microcompartment operon and an enzyme fused to a microcompartment localisation signal, the enzyme capable of converting a low molecular weight substrate into a polymeric or high molecular weight product, the method comprising the steps of:

incubating the recombinant bacteria with the low-molecular weight substrate, or a precursor of the low molecular weight substrate which is capable of being metabolised to the substrate within the recombinant bacteria, such that the substrate or precursor is taken up by the bacteria, wherein the substrate enters the microcompartment and the enzyme within the microcompartment converts the substrate to a polymeric or high molecular weight molecular product, and wherein the polymeric or high molecular weight molecular product is accumulated within the microcompartment. Accumulation is typically due to its size and the fact that it is shielded from native enzymatic metabolic processes otherwise capable acting on it to convert the product to other molecular products.

In one embodiment, the method is a method of removing inorganic phosphate (Pi) from a system such as for example a body of water, or a human or animal body. The method generally employs recombinant bacteria which are transformed to express a microcompartment (metabolosome) operon and a polyphosphate kinase (i.e. PPK1 or a variant thereof) enzyme fused to a microcompartment localisation sequence. The method suitably comprises the steps of incubating the recombinant bacteria with the system such that the recombinant bacteria comes into contact with the Pi (precursor) in the system, wherein Pi from the system is taken up the bacteria as part of normal metabolism for incorporation in the intracellular metabolite adenosine triphosphate. This passes into the bacteria and is metabolised to adenosine triphosphate (substrate) which enters the microcompartment and is converted to a high molecular weight polyphosphate polymer by the polyphosphate kinase (i.e. PPK1) enzyme located within the microcompartment, and wherein the polyphosphate is accumulated within the microcompartment due to its size. The bacterial microcompartment employed in the methods, bacteria, plasmids, and kits of the invention preferably includes pores which are typically dimensioned to allow passage of ATP adenosine triphosphate (substrate) but to prevent passage of PPK1-formed polyphosphate.

In a further embodiment of the invention, there is provided a method of rendering irreversible a metabolic pathway of the type involving enzymatic synthesis of a polymeric or high molecular weight compound, which pathway is normally reversible due to the action of one or more endogenous enzymes, the method comprising a step of:
  accumulating the polymeric or high molecular weight compound within a bacterial microcompartment according to the method described above,
  wherein the microcompartment prevents the or each endogenous enzymes coming into contact with the accumulated polymeric or high molecular weight compound.

In a separate, but linked aspect, the invention provides a recombinant bacteria as defined in the claims. Typically, the recombinant bacteria is transformed to express a bacterial microcompartment operon and an enzyme fused to a bacterial microcompartment localisation signal, the enzyme capable of converting a low molecular weight substrate into a polymeric or high molecular weight product, in which the microcompartment has pores that are dimensioned to allow the low molecular weight substrate pass into the microcompartment and prevent the polymeric or high molecular weight molecular products pass out of the microcompartment.

Typically, the bacteria is transformed to express a microcompartment localisation signal peptide capable of targeting the enzyme to the microcompartment. Suitably, the microcompartment localisation signal is defined by the 18 N-terminal amino acids of NCBI locus CAM57296, GI:171854198, (SEQ ID NO: 4), or a variant thereof having the property of targeting the enzyme (i.e. a PPH enzyme) to a bacterial microcompartment. A variant may be selected from another N-terminal region of native microcompartment-targeted enzymes capable of targeting the enzyme to the congruent microcompartment.

Suitably, the bacteria are transformed to express both the microcompartment and the enzyme.

In a preferred embodiment, the bacterial microcompartment is encoded by an empty microcompartment operon such as that described in Parsons et al. in reference to the Pdu operon structural genes expressed in the order pduABJKNU (hereafter "empty Pdu microcompartment"). Ideally the empty Pdu microcompartment is defined by NCBI loci CAM57283.1 (SEQ ID NO: 5), CAM57284.1 (SEQ ID NO: 6), CAM57290.1 (SEQ ID NO: 7), CAM57291.1 (SEQ ID NO: 8), CAM57294.1 (SEQ ID NO: 9), and CAM57300.1 (SEQ ID NO: 10), respectively, or a variant thereof having the property of being able to form a microcompartment when expressed by a cell.

In an alternative embodiment, the empty bacterial microcompartment is encoded by combining three microcompartment operon structural genes; one encoding a hexamer (PduA-like, CAM57283.1(SEQ ID NO: 5), CAM57290.1 (SEQ ID NO: 7) above) containing a single microcompartment domain (InterPro domain IPR000249), one encoding a trimeric pseudohexameric molecule (PduB-like, CAM57284.1(SEQ ID NO: 6)) containing two such microcompartment domains, and one encoding a distinct microcompartment domain (EutN/CcmL-like InterPro domain IPR004992, CAM57294.1 (SEQ ID NO: 9) above).

In one example, the microcompartment is capable of accumulation of polyphosphate, i.e. having a pore size dimensioned to allow passage of ATP and prevent outward passage of PPK1-formed polyphosphate. As many different bacteria possess native microcompartment operons and native PPK1 enzymes, it is envisaged that gene rearrangement or self cloning of sufficient native microcompartment genes to make an empty microcompartment, with addition of the congruent N-terminal microcompartment targeting signal to the N-terminal of the native PPK1 enzyme, would achieve the same phenotype in many bacteria. C-terminal location of the microcompartment localisation signal relative to the enzyme to be targeted is also effective and may be useful in certain circumstances, depending on the location of the enzyme active site.

The nature of the targeting sequence, an 18 amino acid peptide, means that novel targeting sequences can readily be generated by one skilled in the art using well established functional techniques such as phage display to select random 18-mers capable of binding microcompartment shell proteins. A flexible linking peptide commonly used to separate attachment sites from functional regions of fusion proteins (Sengupta, A., C. K. Thai, M. S. R. Sastry, J. F. Matthaei, D. T. Schwartz, E. J. Davis, and F. Baneyx, *A Genetic Approach for Controlling the Binding and Orientation of Proteins on Nanoparticles*. Langmuir, 2008. 24(5): p. 2000-2008). may be fused to the C-terminal part of the 18-mer between the enzyme and the targeting sequence to preserve function of the fused protein.

In one embodiment, the bacteria may be selected from *Escherichia coli, Lactobacillus, Bifidobacteria, Pseudomonas, Accumilibacter, Thermus thermophilus, Thermosynechococcus, Halomonas* or *Halobacterium* or other salt tolerant species or other bacteria already adapted to function in the system where phosphate uptake is desired.

Suitably, the body of water constituting the system where phosphate uptake is desired may be a river, a lake, a sea, or a reservoir. A waste liquid stream may be, for example, an effluent stream, an industrial waste stream.

The recombinant bacteria is generally transformed with a plasmid, typically a plasmid according to the claims. Suitably, the plasmid comprises a nucleotide sequence encoding an empty Pdu microcompartment, ideally an empty Pdu microcompartment as defined by NCBI loci CAM57283.1 (SEQ ID NO: 5), CAM57284.1 (SEQ ID NO: 6), CAM57290.1 (SEQ ID NO: 7), CAM57291.1 (SEQ ID NO: 8), CAM57294.1 (SEQ ID NO: 9), and CAM57300.1 (SEQ ID NO: 10) or a variant thereof, or a combination of a minimum of three structural types of microcompartment operon structural genes encoding a microcompartment structure, and a nucleotide sequence encoding the PPK1 enzyme, for example an *E. coli* PPK1 enzyme as defined by NCBI locus NP_416996.1, GI:16130426, or SEQ ID NO: 3, or a variant thereof having the polyphosphate kinase activity of the PPK enzyme, fused to a microcompartment localisation signal sequence, for example as defined by SEQ ID NO: 4 or variants thereof.

Alternatively, the nucleotide sequence encoding the empty Pdu microcompartment (such as that defined by NCBI loci CAM57283.1 (SEQ ID NO: 5), CAM57284.1 (SEQ ID NO: 6), CAM57290.1 (SEQ ID NO: 7), CAM57291.1 (SEQ ID NO: 8), CAM57294.1 (SEQ ID NO: 9), and CAM57300.1 (SEQ ID NO: 10), or a variant thereof, or containing the three structural types of microcompartment shell proteins defined above, capable of accumulating polyphosphate), and the nucleotide sequence encoding the PPK1 enzyme (such as that defined by SEQ ID NO: 3), or variants thereof defined in SEQ ID NO:12-16, are encoded on separate plasmids. The nucleic acid sequence encoding the microcompartment localisation signal peptide is generally located on the same plasmid as the nucleic acid sequence encoding the enzyme so that a fusion protein of the two encoded peptides is produced. Gene insertion in the chromosome of the recombinant bacteria is also envisaged. Because many bacteria already possess genes encoding both microcompartment structural proteins and PPK1, rearrangement of these pre-existing chromosomal genes with the insertion of the cognate microcompartment localisation sequence N-terminal to the native ppk1 would be possible.

Suitably, the bacteria is selected from *Escherichia coli, Lactobacillus, Pseudomonas, Acinetobacter, Accumilibacter*, and *Bacillus*. In an embodiment of the invention in which the recombinant bacteria is intended to be administered to a human, the bacteria will be a food grade bacteria, for example a probiotic bacteria such as a lactobacillus. Details of food-grade and probiotic bacteria will be well known to those skilled in the art.

Suitably, the bacteria is selected from *Escherichia coli, Lactobacillus*, (*L. reuteri. L. acidophilus, L. casei, L. plantarum, L. johnsonii, L. rhamnosus*) *Lactococcus lactis, Bifidobacteria* (*B. infantis, B. breve, B. longum, Bifidobacterium animalis* ssp. *Lactis*), *Enterococcus faecalis, E. faecium*), *Streptoccus thermophilus, Pseudomonas, Accumilibacter*, or other *Proteobacteria, Bacteroidetes, Planctomycetales Firmicutes* or *Actinobacteria* species.

In one embodiment, the recombinant bacteria is transformed to express a microcompartment (metabolosome) containing polyphosphate kinase (PPK1) enzyme, in which the microcompartment has pores that are dimensioned to allow inorganic phosphate pass into the microcompartment and prevent PPK1-formed polyphosphate pass out of the microcompartment. Generally, the PPK1 enzyme is the only metabolic enzyme contained within the microcompartment, normal cytoplasmic enzymes which breakdown polyphosphate (e.g. exopolyphosphatase, PPX), or other polymerising/depolymerising enzymes, are excluded.

Suitably, the bacteria is transformed to express a microcompartment localisation signal peptide which targets the enzyme to the microcompartment In one embodiment, the microcompartment localisation signal is defined by SEQ ID NO: 4, or a variant thereof capable of targeting the enzyme to the microcompartment.

In one embodiment, the invention also relates to a recombinant bacteria of the invention for use as a medicament.

The invention also relates to a recombinant bacteria of the invention, for use in treating a disease or condition associated with accumulation of dietary phosphate, wherein the recombinant bacteria is a food grade bacteria. Typically, the disease or condition is selected from the group consisting of chronic renal disease, acute vitamin D intoxication, hypoparathyroidism, rhabdomyolysis, tumor lysis syndrome, or excessive oral sodium phosphate administration for bowel preparation prior to colonoscopy or barium enema. In one embodiment, the renal disease is selected from the group comprising: Horseshoe kidney; Polycystic kidney disease; Renal dysplasia; Unilateral small kidney; Diabetic nephropathy; Glomerulonephritis; Hydronephrosis; Interstitial nephritis; Lupus nephritis; nephrotic syndrome; and acute renal failure due to excessive phosphate ingestion; chronic renal failure.

The invention also relates to a pharmaceutical composition comprising a recombinant bacteria of the invention in combination with a suitable pharmaceutical excipient.

The invention also relates to a plasmid, or kit of parts, according to the claims. Typically, the plasmid comprises a nucleic acid sequence encoding an enzyme capable of converting a low molecular weight substrate into a polymeric or high molecular weight molecular product, and a nucleic acid sequence encoding a microcompartment localisation signal, the plasmid being capable of expressing a fusion protein comprising the enzyme and the microcompartment localisation signal. Typically, the enzyme is PPK1 and the signal is located at an N-terminal of the PPK1 enzyme.

Typically, the PPK1 gene is defined by SEQ ID NO: 3, or variants thereof having PPK1 activity, and the microcompartment localisation signal is defined by SEQ ID NO: 4, or variants thereof having the property of the microcompartment localisation signal encoded by SEQ ID NO: 4.

Suitably, the plasmid comprises a nucleic acid sequence expressing a microcompartment. Typically, the microcompartment is an empty Pdu microcompartment, such as that encoded by NCBI loci CAM57283.1 (SEQ ID NO: 5), CAM57284.1 (SEQ ID NO: 6), CAM57290.1 (SEQ ID NO: 7), CAM57291.1 (SEQ ID NO: 8), CAM57294.1 (SEQ ID NO: 9), and CAM57300.1 (SEQ ID NO: 10) or variants thereof encoding a microcompartment having the properties of a Pdu microcompartment.

The invention also provides the plasmid comprising a PPK1 gene and a nucleic acid encoding a microcompartment localisation signal, in combination with a separate plasmid expressing a microcompartment. Typically, the microcompartment is an empty Pdu microcompartment encoded by NCBI loci CAM57283.1 (SEQ ID NO: 5), CAM57284.1 (SEQ ID NO: 6), CAM57290.1 (SEQ ID NO: 7), CAM57291.1 (SEQ ID NO: 8), CAM57294.1 (SEQ ID NO: 9), and CAM57300.1 (SEQ ID NO: 10) or variants thereof encoding a microcompartment having the properties of a Pdu microcompartment.

DEFINITIONS

As used herein, a variant is intended to mean a substantially similar sequence. For polynucleotides, a variant comprises a substitution of one or more nucleotides at one or more sites in the native polynucleotide, and/or a deletion and/or addition of one or more nucleotides at one or more internal sites within the native polynucleotide. One of skill in the art will recognise that variants of the nucleic acid of the invention will be constructed such that the open reading frame is maintained. Generally, variants of a particular polynucleotide of the invention will have at least about 30%, 35%, 40% 45%, 50%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programmes. A variant of PPK1 is a protein having at least 70%, 75%, 80%, 85%, 90%, 95%, 96%, 97%, 98%, 99% sequence identity with SEQ ID NO: 3 as determined by sequence alignment programmes, for example BLAST.

Variant protein is intended to mean proteins derived from the native protein by addition of deletion of one or more amino acids at one or more internal site in the native proteins and/or substitution of one or more amino acids at one or more sites in the native protein. Variant proteins are biologically active, that is they continue to possess the desired biological activity of the native protein. Variants may result from genetic polymorphism or from human manipulation. Biologically active variants of a native microcompartment localisation sequence, or microcompartment shell protein, or PPK1 enzyme or CphA enzyme of the invention will have at least about 30%, 35%, 40% 45%, 50%, 60%, 65%, 70%, 75%, 80%, 85%, or more preferably 90%, 91%, 92%, 93%, 94%, 95%, 96%, 97%, 98%, 99% or more sequence identity to the amino acid sequence for the native proteins as determined by sequence alignment programmes (such as BLAST).

In the specification, the term "transformed" should be understood to mean bacterial transformation which is a stable genetic change brought about by the uptake of naked DNA (DNA without associated cells or proteins) and competence refers to the state of being able to take up exogenous DNA from the environment. Artificial competence can be induced in laboratory procedures that involve making the cell passively permeable to DNA by exposing it to conditions that do not normally occur in nature. Such transformation procedures are known to the skilled person, such as, for example, calcium chloride transformation or electroporation.

Unless stated otherwise, the term "microcompartment" should be understood to mean "bacterial microcompartment" and the term "microcompartment localisation signal" should be understood to mean "bacterial microcompartment localisation signal".

BRIEF DESCRIPTION OF THE DRAWINGS

The invention will be more clearly understood from the following description of an embodiment thereof, given by way of example only, with reference to the accompanying drawings, in which:

FIG. 3 illustrates (a) Phosphate removal and (b) polyphosphate accumulation.

Figure 1A:
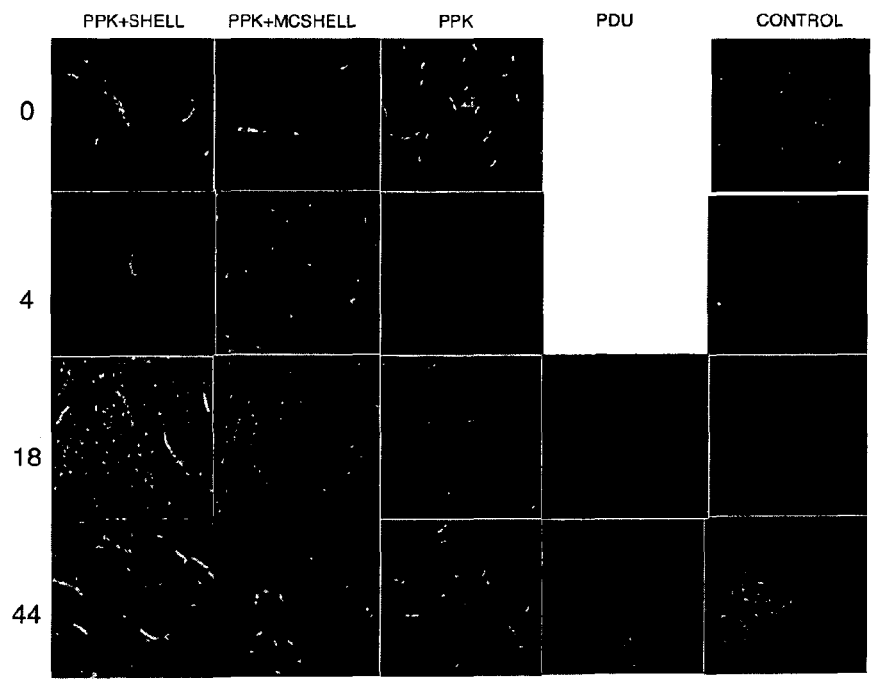
FIG. 1A illustrates a series of fluorescent microscopy image of bacteria in MOPS captured at 0, 4, 18 and 44 hours incubation in MOPS buffer; induction time of ppk is at −1 hours.
Figure 1B:
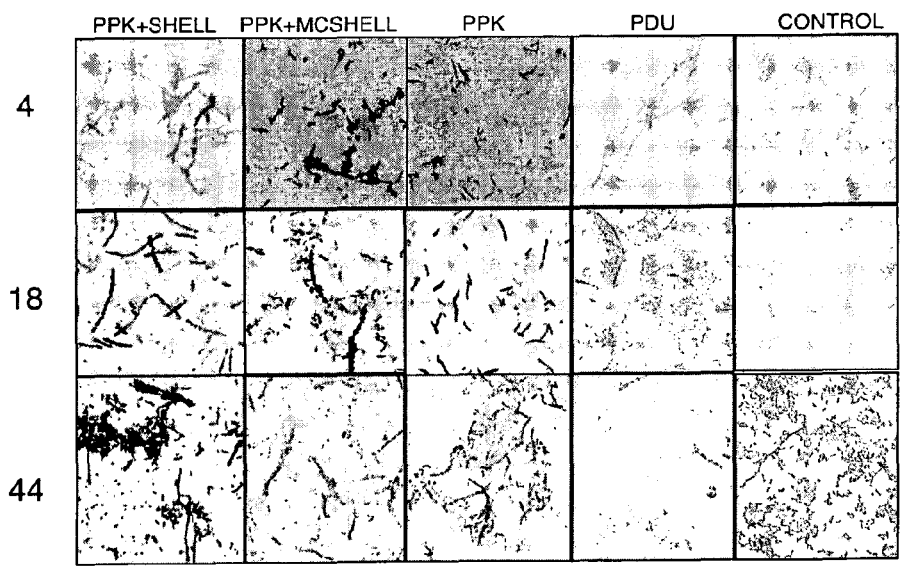
FIG. 1B illustrates Neisser's stain (Toluidine blue with chrysoidine counterstain) of fixed films of *E. coli* clones captured at 4, 18 and 44 hours incubation in MOPS buffer; induction time of ppk is at −1 hours. Fluorescence microscopy (FIG. 1A) demonstrated the presence of large yellow fluorescent granules in tetracycline-stained *E. coli* cells containing the cloned pdu structural operon and ppk gene and localisation signal (lppk/pdu). Smaller granules were seen in *E. coli* containing the ppk gene alone. Intracellular polyphosphate was detected in clones over-expressing ppk by light microscopy with Neisser's stain (FIG. 1B—PPK). Blue black granules were also apparent with Neisser's stain in a proportion of all cells containing a cloned ppk gene, but not the *E. coli* BL21 insert-free control or the pdu-only clone (FIG. 1B). These appearances are consistent with the accumulation of intracellular polyphosphate in cells with increased ppk activity. The lppk/pdu clones retained the polyphosphate staining at 44 hours (FIGS. 1A and 1B) whereas the ppk only clone showed reduced staining at 44 hours (FIG. 1B). More intracellular polyphosphate was observed at 44 hours in the lppk/pdu ppk clone (FIG. 1B—PPK1+SHELL). All clones containing ppk showed a heterogeneous granule phenotype, with a proportion of non-fluorescing or non-toluidine blue staining cells in all fields.
Figure 2:
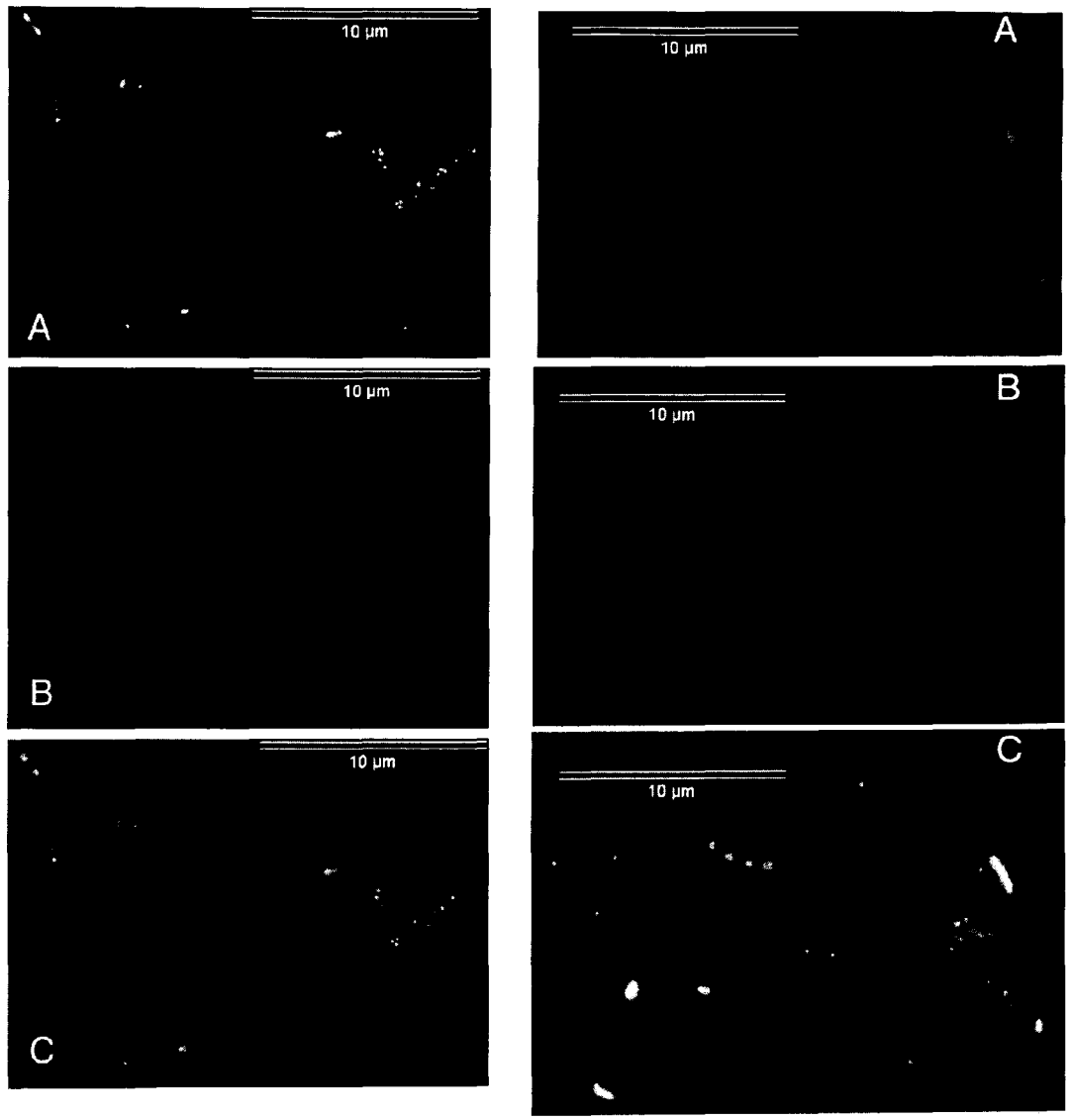
FIG. 2 illustrates Fluorescent Microscopy Localisation (i). 18 hours post ppk induction and (ii) 44 hours post induction. 'A' represents Tetracycline stain (yellow-green polyphosphate), 'B' represents MCherry Fluorescence, while 'C' represents an overlay of 'A' and 'B'. All pdu operon containing clones had a proportion of cells which were greatly elongated. Granules of the PPK1 metabolic product polyphosphate lie within MCherry labelled microcompartment protein (FIG. 2), and microcompartment extractions show the presence of PPK1. Some of the cells in all clones forming multiple polyphosphate granules tended to be larger than the non-granulate cells, presumably because of distension by the granules. However, the largest cells were seen with the combination of pdu and ppk. MCherry labelled PduA was observed to enclose polyphosphate visualised with tetracycline fluorescence (FIG. 2, Panels A and B). At earlier incubations (FIG. 2, Panels A) the MCherry labelled protein was in excess (the pdu operon is constitutively expressed from the plasmid before ppk induction occurs), but at 48 hours (FIG. 2, Panels B) the co-location of MCherry and polyphosphate was more obvious. Intracellular polyphosphate was detected in clones over-expressing ppk by fluorescent microscopy with tetracycline staining (FIG. 2—Panel B). There was heterogeneity in MCherry labelling and the presence of polyphosphate granules in the MCherry and lppk/pdu clones. The lppk/pdu clones retained the polyphosphate staining at 44 hours (FIG. 2, Panels A and B).
Figure 3A:
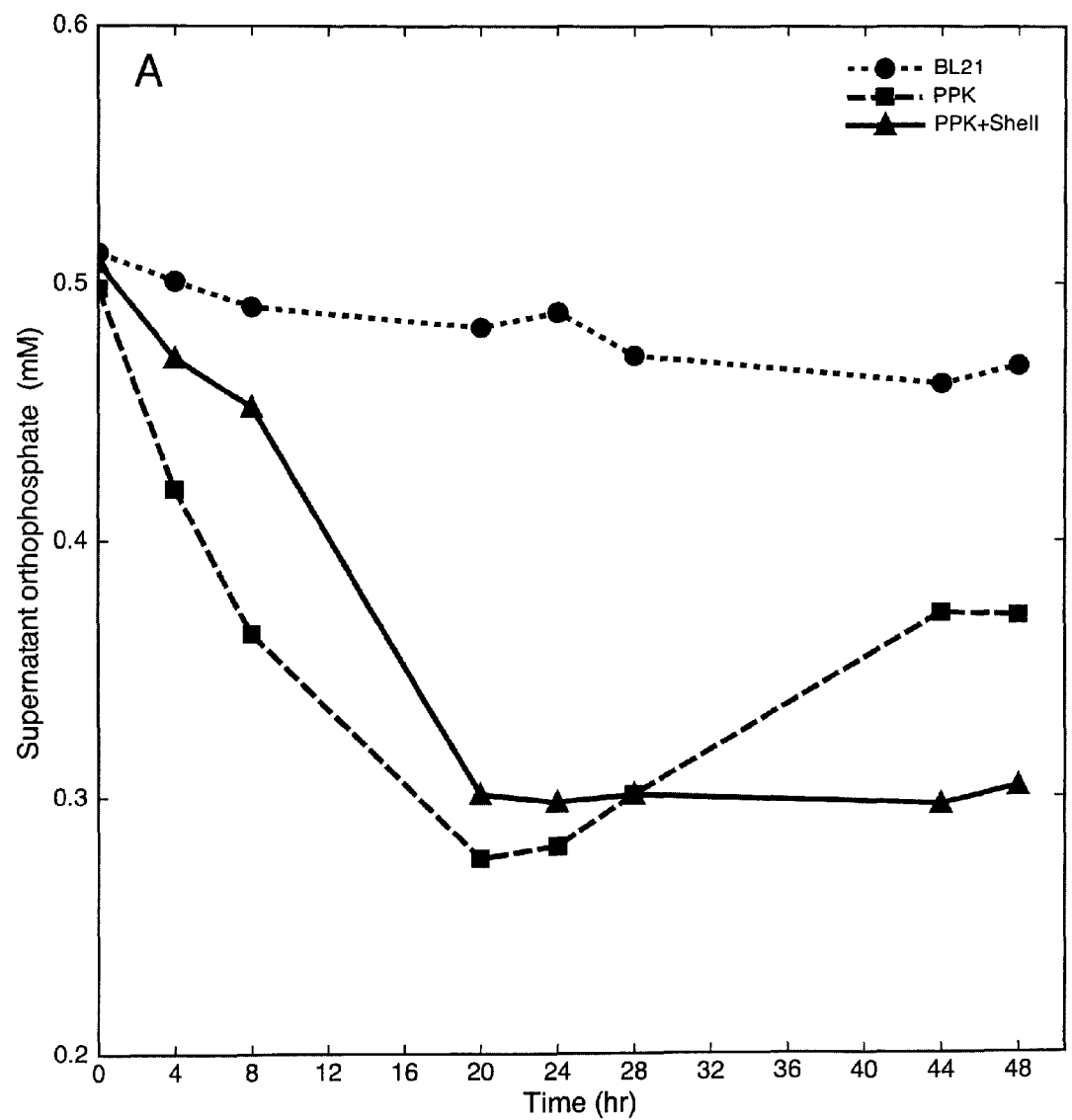
Referring now to FIGS. 3A and 3B, increased phosphate uptake from culture medium compared with the host *E. coli* control was displayed by both the ppk clone (square symbol) and the clone with both a pdu structural operon and a ppk gene with a localisation signal (lppk/pdu) (triangle symbol), reaching a maximal uptake of approximately 0.2 mM at 20 hours for both constructs. However, the ppk clone returned approximately 50% of this phosphate to the supernatant after 44 hours, while the lppk/pdu clone retained approximately 100% of the phosphate taken up for at least 48 hours. Correspondingly, the cell-associated polyphosphate levels of the ppk clone were maximal at 20 hours and declined thereafter, while the lppk/pdu clone retained the same level of cell-associated polyphosphate at 48 hours as at 20 hours.
Figure 3B:
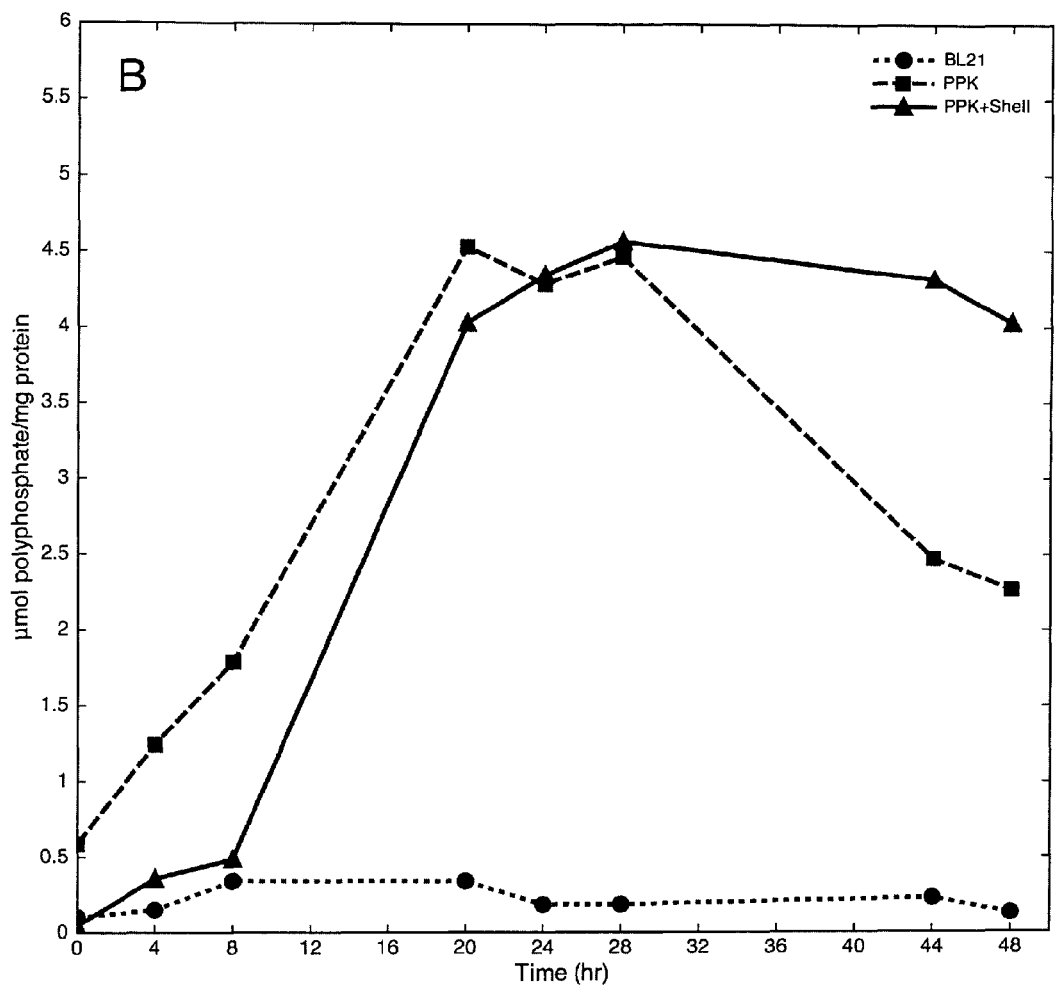

The results presented herein illustrate that the enclosure of PPK within a bacterial microcompartment still allows access of the small molecule substrate ATP to the enzyme, but effectively stabilises the large polymer polyphosphate product by retaining it in the interior of the microcompartment, presumably by preventing access of PPX, GPPA or other cytoplasmic phosphatases. In this way, a metabolic pathway which is reversible in vivo by the action of competing enzymes has been converted to an irreversible pathway by removing access of the competing enzyme to the metabolic product. Because of the apparent instability of cytoplasmic polyphosphate accumulation even in ppk containing organisms, presumably due to competing enzymes breaking down polyphosphate, wastewater treatment plants currently using enhanced biological phosphorus removal (EBPR) employ a cycling process. In EBPR, a community of microorganisms, usually including a dominant phosphate-retaining uncultivated organism, *Accumilibacter phosphatis*, incubated in aerobic conditions takes up phosphate for storage as polyphosphate, and then during anaerobic incubation releases phosphate from polyphosphate stores. Incremental net phosphate uptake occurs due to a slight excess of aerobic uptake over anaerobic release. A requirement for cycling environmental conditions places a restriction on the application of EBPR, for example during transit through the intestine it would be difficult to arrange, even if acceptable bacteria for oral administration could be identified.

It has been shown here that localisation of an enzyme with a short N-terminal sequence to the interior of a bacterial microcompartment can affect turnover of the product of the reaction catalysed by the enzyme, presumably due to restriction of access for competing enzymes acting on the metabolic product. Toxic metabolic products could also be similarly compartmentalised.

DETAILED DESCRIPTION OF THE DRAWINGS

The use of compartmentalisation by microcompartments to manipulate metabolic pathways rendering reversible cellular reactions irreversible, and engineer novel metabolites is described herein.

TABLE 1

Molecular weights of native microcompartment enzyme substrates and products, and polymeric products of recombinant enzymes targeted to microcompartments.

| Process | Enzyme | Substrate (MW, g/mol) | Product (MW, g/mol) |
| --- | --- | --- | --- |
| Native Propanediol utilisation (1) | | | |
| | Diol dehydratase PduCDE | 1,2-propanediol (76.09) | Propionaldehyde (58.08) |
| | Diol dehydratase PduCDE | Glycerol (92.09) | 3-hydroxy-propionaldehyde (74.078) |
| | Propionaldehyde dehydrogenase PduP | Propionaldehyde (58.08) Co-enzyme A (767.54) | Propionyl-CoA (823.6) |
| Native Ethanolamine utilisation (2) | | | |
| | Ethanolamine deaminase EutBC | Ethanolamine (61.08) | Acetaldehyde (44.05) |
| | Acetaldehyde dehydrogenase EutE | Acetaldehyde (44.05) Co-enzyme A (767.54) | Acetyl-CoA (809.57) |
| | Alcohol dehydrogenase EutG | Acetaldehyde (44.05) | Ethanol (46.068) |
| Recombinant polyphosphate formation | | | |
| | Polyphosphate kinase PPK1 | ATP (507.18) | Polyphosphate polymer |

TABLE 1-continued

Molecular weights of native microcompartment enzyme substrates and products, and polymeric products of recombinant enzymes targeted to microcompartments.

Figure 4:
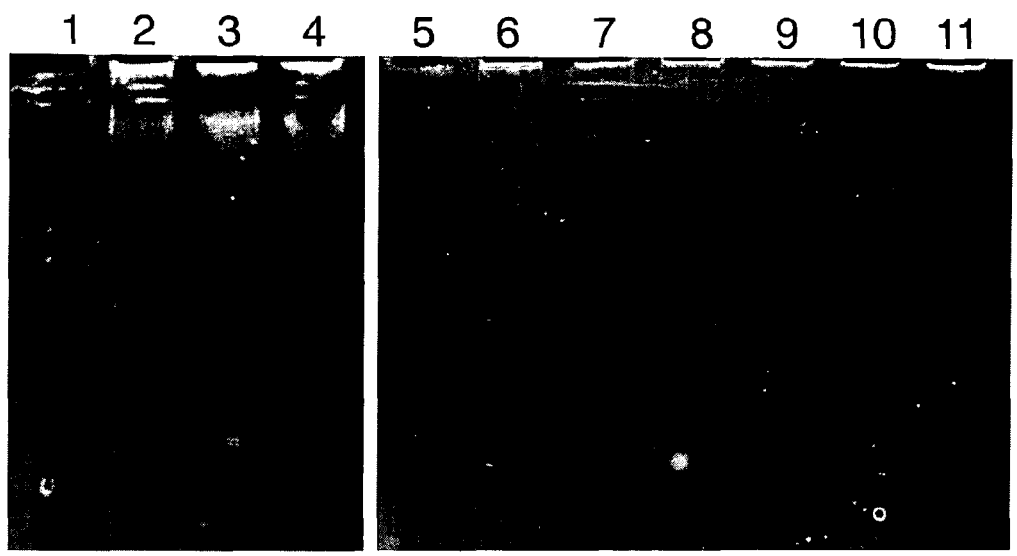
FIG. 4 illustrates the size distribution of extracted polyphosphate. A DAPI PAGE gel of polyphosphate extractions quantified in FIG. 2. Polyphosphate associated with DAPI is bleached by prior UV exposure and appears as a dark band. High molecular weight shadows below the inoculation well correspond to lipid (extracts treated with micrococcal nuclease to remove DNA). Lanes 1 and 5: Sodium phosphate glass Type 45 (Sigma). Lanes 2, 3, 4: Time zero extractions. Lane 6, 7, 8: time 24 hours. Lanes 9, 10, 11: time 48 hours. Lanes 2, 6, 9: *E. coli* BL21. Lanes 3, 7, 10: *E. coli* BL21 ppk. Lanes 4, 8, 11: *E. coli* lppk/pdu. DAPI negative staining of polyphosphate extracts size-separated on a PAGE gel (FIG. 4) showed that the polyphosphate detected in both ppk and lppk/pdu clones exceeded the length of the sodium phosphate glass Type 45 control and was therefore in long chains; that is as long-chain polyphosphate molecules. No qualitative difference in chain length was detected between ppk and lppk/pdu clones. No long chain polyphosphate was detected in the *E. coli* control.
Figure 5:
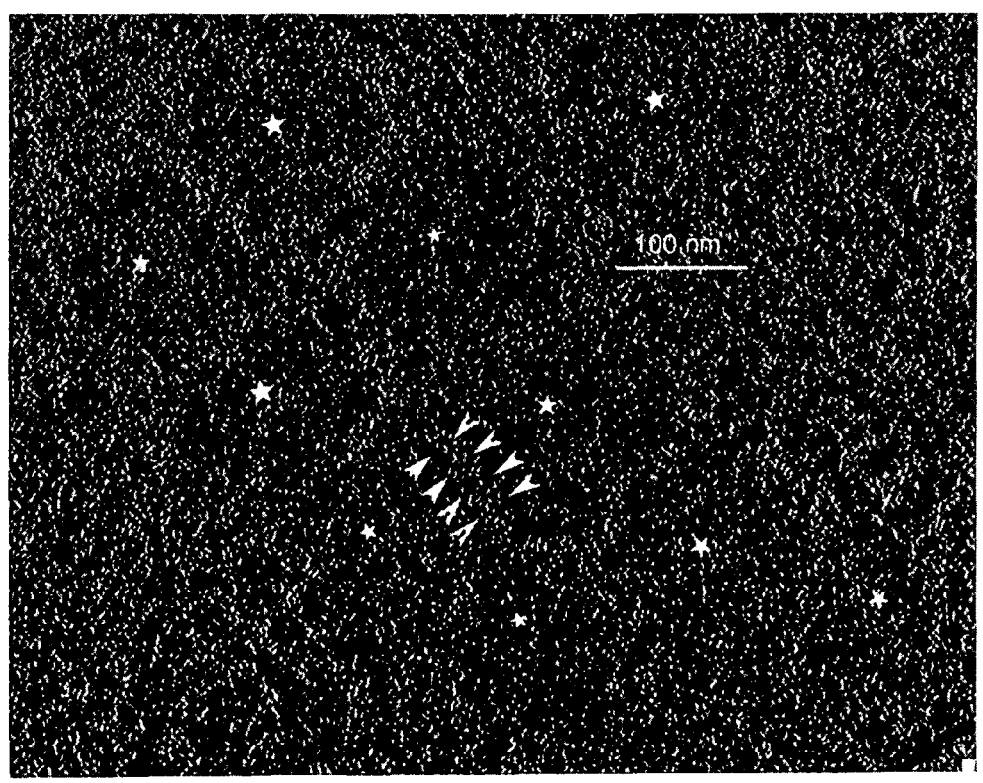
FIG. 5 illustrates the shape of presumed polyphosphate granules in the *E. coli* clone containing both a pdu structural operon and a ppk gene with a localisation signal (lppk/pdu). The light microscopy appearance of this clone in the same incubation conditions (shown in FIGS. 1A and 1B as PPK+ Shell) shows extensive polyphosphate granules. This section of a tomogram constructed using images from a cryoelectron microscope shows electron dense material resembling polyphosphate granules (white asterisks) in polygonal clusters of approximately uniform size 120-150 nm in diameter. Although obvious shell structures surrounding entire polyphosphate granules are not apparent with the resolution of this tomogram, in this tomographic section there is a clear linear separation of adjacent clusters by less electron dense material (white arrowheads), representative of planes of separation visible in the tomographic reconstruction. This suggests enclosure of polyphosphate by a distinct, less electron dense material. These appearances are unlike previously published cryoelectron microscopy tomographic appearances of intracellular polyphosphate granules, which were isolated, often spherical and much more variable in size. The restriction of polyphosphate granules to uniform polygonal shapes with clear planar demarcation between adjacent bodies suggests polyphosphate is being formed inside the containment of a polygonal microcompartment shell.
Figure 6:
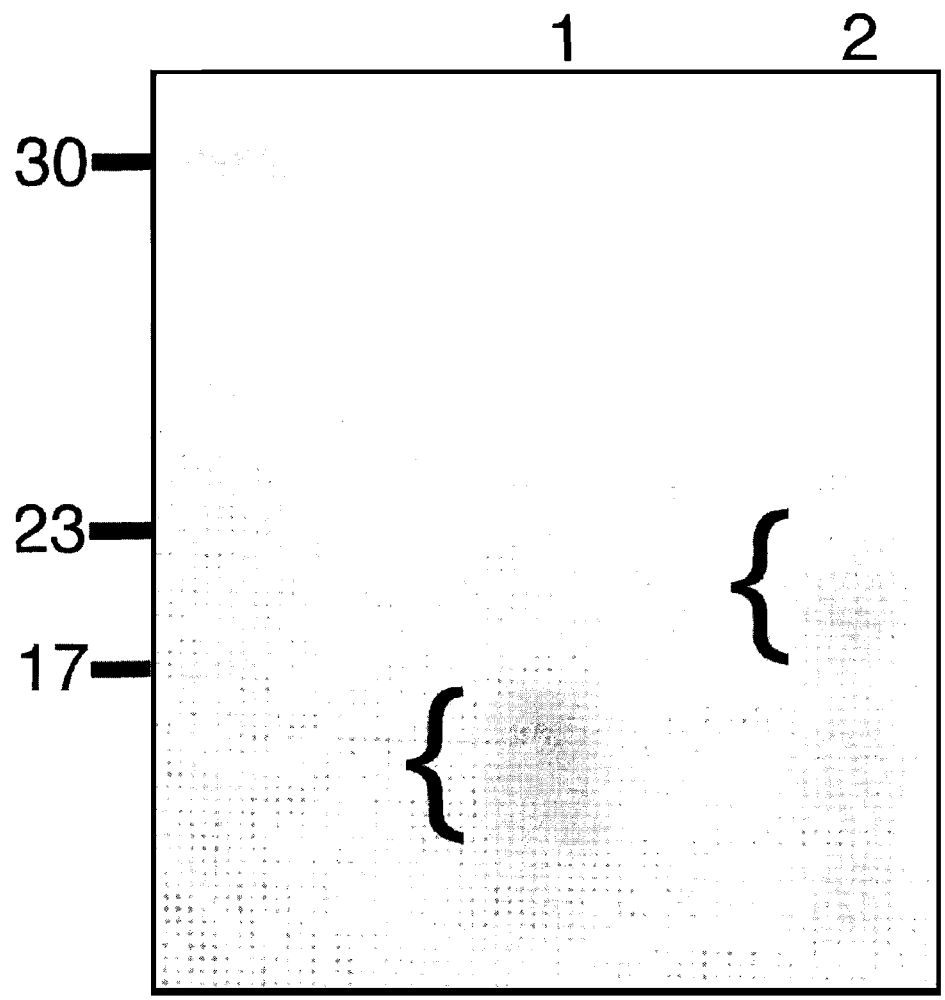
FIG. 6 illustrates the effect of cloning the pdu structural operon and expressing cphA cyanophycin synthetase in *E. coli*. A Western Blot is provided where Lane 1 contains an extract from cells expressing cphA, and lane 2 CphA with a localisation signal and a pdu structural operon (empty microcompartment). An increase in molecular weight of the predominant band is noted from 16-18 kD to 17-23 kDa.

| Process | Enzyme | Substrate (MW, g/mol) | Product (MW, g/mol) |
|---|---|---|---|
|  |  |  | 50,000-80,000 (500-800 phosphate monomers 94.97) (FIG. 4) |
| Recombinant cyanophycin synthesis |  |  |  |
|  | Cyanophycin synthetase CphA | Aspartic acid (133.11) Arginine (174.2) | Cyanophycin polymer (20-30,000) (FIG. 5) |

1. Havemann, G. D. and T. A. Bobik, Protein content of polyhedral organelles involved in coenzyme B12-dependent degradation of 1,2-propanediol in *Salmonella enterica* serovar Typhimurium LT2. J Bacteriol, 2003. 185(17): p. 5086-95.
2. Brinsmade, S. R., T. Paldon, and J. C. Escalante-Semerena, Minimal functions and physiological conditions required for growth of *salmonella enterica* on ethanolamine in the absence of the metabolosome. J Bacteriol, 2005. 187(23): p. 8039-46.

Methods
Strains and Plasmids

TABLE 2

Plasmids, Strains and their sources used

| | Source |
|---|---|
| Plasmids | |
| pET23b | Novagen |
| pET23b-GFPpduP18 | Prof. Martin Warren, University of Kent |
| pET23bpduP18-ppk (pYY001) | This study |
| pLysSPduABJKNY | Parsons J. et al. * |
| pLysSmcherryPduABJKNU | " |
| Strains | |
| *E. coli* JM109 | Promega |
| *E. coli* Top 10 | Invitrogen |
| *E. coli* BL21 (DE3) | Stratagene |

* Parsons, J., S. Frank, D. Bhella, M. Liang, M. B. Prentice, D. Mulvihill, and M. J. Warren, Synthesis of Empty Bacterial Microcompartments, Directed Organelle Protein Incorporation, and Evidence of Filament-Associated Organelle Movement. Molecular Cell, 2010. 38: p. 305-315.

Media

MOPS medium was as described (Neidhardt, F. C., P. L. Bloch, and D. F. Smith, *Culture Medium for Enterobacteria*. J. Bacteriol., 1974. 119(3): p. 736-747) with either $K_2HPO_4$ 0.5 mM or 1.0 mM.

The ppk gene coding for polyphosphate kinase (PPK1) was PCR-amplified with Taq using genomic DNA from *E. coli* JM109 as template, using the forward primer (5-AGT GAG CTC ATG GGT CAG GAA AAG CTA TAC ATC GAA AAA GAA CTC-3—SEQ ID NO: 1) and a reverse primer (5-AAT AAA GCT TTT ATT CAG GTT GTT CGA G-3—SEQ ID NO. 2). The PCR product was digested with Sac I and Hind III (Fermentas) followed by ligation to pET23b-GFP-pduP18 digested with Sac I and Hind III. The gfp gene was thus replaced by ppk with retention of the pdu localization sequence.

```
SEQ ID NO: 3 ppk sequence:
ATGGGTCAGGAAAAGCTATACATCGAAAAAGAACTCAGTTGGTTAT

CGTTCAATGAACGCGTGCTTCAGGAAGCGGCGGACAAATCTAACCC
```
-continued
```
GCTGATTGAAAGGATGCGTTTCCTGGGGATCTATTCCAATAACCTT

GATGAGTTCTATAAAGTCCGCTTCGCTGAACTGAAGCGACGCATCA

TTATTAGCGAAGAACAAGGCTCCAACTCTCATTCCCGCCATTTACT

GGGCAAAATTCAGTCCCGGGTGCTGAAAGCCGATCAGGAATTCGAC

GGCCTCTACAACGAGCTATTGCTGGAGATGGCGCGCAACCAGATCT

TCCTGATTAATGAACGCCAGCTCTCCGTCAATCAACAAAACTGGCT

GCGTCATTATTTTAAGCAGTATCTGCGTCAGCACATTACGCCGATT

TTAATCAATCCTGACACTGACTTAGTGCAGTTCCTGAAAGATGATT

ACACCTATCTGGCGGTGGAAATTATCCGTGGCGATACCATCCGTTA

CGCGCTGCTGGAGATCCCATCAGATAAAGTGCCGCGCTTTGTGAAT

TTACCGCCAGAAGCGCCGCGTCGACGCAAGCCGATGATTCTTCTGG

ATAACATTCTGCGTTACTGCCTTGATGATATTTTCAAAGGCTTCTT

TGATTATGACGCGCTGAATGCCTATTCAATGAAGATGACCCGCGAT

GCCGAATACGATTTAGTGCATGAGATGGAAGCCAGCCTGATGGAGT

TGATGTCTTCCAGTCTCAAGCAGCGTTTAACTGCTGAGCCGGTGCG

TTTTGTTTATCAGCGCGATATGCCCAATGCGCTGGTTGAAGTGTTA

CGCGAAAAACTGACTATTTCCCGCTACGACTCCATCGTCCCGGCG

GTCGTTATCATAATTTTAAAGACTTTATTAATTTCCCCAATGTCGG

CAAAGCCAATCTGGTGAACAAACCACTGCCGCGTTTACGCCATATT

TGGTTTGATAAAGCCCAGTTCCGCAATGGTTTTGATGCCATTCGCG

AACGCGATGTGTTGCTCTATTATCCTTATCACACCTTTGAGCATGT

GCTGGAACTGCTGCGTCAGGCTTCGTTCGACCCGAGCGTACTGGCG

ATTAAAATTAACATTTACCGCGTGGCGAAAGATTCACGCATCATCG

ACTCGATGATCCACGCCGCACATAACGGTAAGAAAGTCACCGTGGT

GGTTGAGTTACAGGCGCGTTTCGACGAAGAAGCCAACATTCACTGG

GCGAAGCGCCTGACCGAAGCAGGCGTGCACGTTATCTTCTCTGCGC

CGGGGCTGAAAATTCACGCCAAACTGTTCCTGATTTCACGTAAAGA
```

-continued

```
AAACGGTGAAGTGGTGCGTTATGCACACATCGGGACCGGGAACTTT
AACGAAAAAACCGCGCGTCTTTATACTGACTATTCGTTGCTGACCG
CCGATGCGCGCATCACCAACGAAGTACGGCGGGTATTTAACTTTAT
TGAAAACCCATACCGTCCGGTGACATTTGATTATTTAATGGTATCG
CCGCAAAACTCCCGCCGCCTATTGTATGAAATGGTGGACCGCGAGA
TCGCCAACGCGCAGCAAGGGCTGCCCAGTGGTATCACCCTGAAGCT
AAATAACCTTGTCGATAAAGGCCTGGTTGATCGTCTGTATGCGGCC
TCCAGCTCCGGCGTACCGGTTAATCTGCTGGTTCGCGGAATGTGTT
CGCTGATCCCCAATCTGGAAGGCATTAGCGACAACATTCGTGCCAT
CAGTATTGTTGACCGTTACCTTGAACATGACCGGGTTTATATTTTT
GAAAATGGCGGCGATAAAAAGGTCTACCTTTCTTCCGCCGACTGGA
TGACGCGCAATATTGATTATCGTATTGAAGTGGCGACGCCGCTGCT
CGATCCGCGCCTGAAGCAGCGGGTACTGGACATCATCGACATATTG
TTCAGCGATACGGTCAAAGCACGTTATATCGATAAAGAACTCAGTA
ATCGCTACGTTCCCCGCGGCAATCGCCGCAAAGTACGGGCGCAGTT
GGCGATTTATGACTACATCAAATCACTCGAACAACCTGAATAAAAG
CTTG
```

SEQ ID NO: 4 pdu localisation sequence
MNTSELETLIRNILSEQLA

SEQ ID NO: 11 Cyanophycin synthase CphA from
Geminocystis herdmanii(Synechocystis sp) strain
PCC6308 (UniProt P56947, EMBL-CDS: AAF43647.2):

MKILKTQTLRGPNYWSIRRQKLIQMRLDLEDVAEKPSNLIPGFYEG
LVKILPSLVEHFCSRDHRGGFLERVQEGTYMGHIVEHIALELQELA
GMPVGFGRTRETSTPGIYNVVFEYVYEEAGRYAGRVAVRLCNSIIT
TGAYGLDELAQDLSDLKDLRANSALGPSTETIIKEAEARQIPWMLL
SARAMVQLGYGANQQRIQATLSNKTGILGVELACDKEGTKTTLAEA
GIPVPRGTVIYYADELADAIADVGGYPIVLKPLDGNHGRGITIDIN
SQQEAEEAYDLASAASKTRSVIVERYYKGNDHRVLVINGKLVAVSE
RIPAHVTGNGSSTIEELIQETNEHPDRGDGHDNVLTRISIDRTSLG
VLKRQGFEMDTVLKKGEVAYLRATANLSTGGIAIDRTDEIHPQNIV
VIAERVAKIIGLDIAGIDVVTPDITKPLTEVDGVIVEVNAAPGFRM
HVAPSQGLPRNVAAPVIDMLFPDNHPSRIPILAVTGTNGKTTTTRL
LAHIYRQTGKVVGYTSTDGIYLGDYMVEKGDNTGPVSAGVILRDPT
VEVAVLECARGGILRSGLAFESCDVGVVLNVAEDHLGLGDIDTIEQ
MAKVKGVIAESVNADGYAVLNADDPLVAQMAKNVGKIAYFSMSKD
NPIIIDHLRRNGMAAVYENGYLSIFEGEWTLRIEKAENIPVTMKAM
APFMIANALAASLAAFVHGIDIELIRQGVRSFNPGANQTPGRMNLF
DMKDFSVLIDYAHNPAGYLAVGSFVKNWKGDRLGVIGGPGDRRDED
LMLLGKIASQIFDHIIIKEDDDNRGRDRGTVADLIAKGIVAENPNA
SYDDILDETEAIETGLKKVDKGGLVVIFPESVTGSIEMIEKYHLSS
E
```

SEQ ID NO: 12 >gi|13878615|sp|O25654.1|
PPK_HELPY

MNRFFNRELSWLAFNTRVLNEAKDESLPLLERLKFLAIYDTNLDEF
YMIRVAGLKQLYEHKIASKGIDGASPEEQLEKIKHYLAHEIEEREL
EFQKIQALLFKKGLCITPYNELNLEQKAKAKTYFKEQLYALVLPFK
LDSSHTFPPLANLTFALFARIKDKETQIISYALIKLPSFIFRFVEL
EKGLFVLAEEIVEAHLEELFLEHEILDCMAFRVTCDADIAITEDEA
HDYADLMSKSLRKRNQGEIVRLQTQKGSQELLKTLLASLRSFQTHS
YKKHKLTGMHIYKSAIMLNLGDLWELVNHSDFKALKSPNFTPKIHP
HFNENDLFKSIEKQDLLLFHPYESFEPVIDLIEQAASDPATLSIKM
TLYRVGKHSPIVKALIEAASKIQVSVLVELKARFDEESNLHWAKAL
ERAGALVVYGVFKLKVHAKMLLITKKTDNQLRHFTHLSTGNYNPLS
AKVYTDVSFFSAKNEIANDIIKLFHSLLTSSATNSALETLFMAPKQ
IKPKIIELIQNEMNHQQEGYIILKANALVDSEIIEWLYQASQKGVK
IDLIIRGICCLKPQVKGLSENIRVYSIVGKYLEHARIYYFKHENIY
FSSADLMPRNLERRVELLIPATNPKIAHKLLHILEIQLKDTLKRYE
LNSKGRYIKVSNPNDPLNSQDYFEKQALKTF

SEQ ID NO: 13 >gi|157217220|ref|YP_001463823.1|
polyphosphate kinase [Escherichia coli E24377A]

MGQEKLYIEKELSWLSFNERVLQEAADKSNPLIERMRFLGIYSNLL
DEFYKVRFAELKRRIIISEEQGSNSHSRHLLGKIQSRVLKADQEFD
GLYNELLLEMARNQIFLINERQLSVNQQNWLRHYFKQYLRQHITPI
LINPDTDLVQFLKDDYTYLAVEIIRGDTIRYALLEIPSDKVPRFVN
LPPEAPRRRKPMILLDNILRYCLDDIFKGFFDYDALNAYSMKMTRD
AEYDLVHEMEASLMELMSSSLKQRLTAEPVRFVYQRDMPNALVEVL
REKLTISRYDSIVPGGRYHNFKDFINFPNVGKANLVNKPLPRLRHI
VVFDKAQFRNGFDAIRERDVLLYYPYHTFEHVLELLRQASFDPSVL
AIKINIYRVAKDSRIIDSMIHAAHNGKKVTVVVELQARFDEEANIH
WAKRLTEAGVHVIFSAPGLKIHAKLFLISRKENGEVVRYAHIGTGN
FNEKTARLYTDYSLLTADARITNEVRRVFNFIENPYRPVTFDYLMV
SPQNSRRLLYEMVDREIANAQQGLPSGITLKLNNLVDKGLVDRLYA
ASSSGVPVNLLVRGMCSLIPNLEGISDNIRAISIVDRYLEHDRVYI
FENGGDKKVYLSSADWMTRNIDYRIEVATPLLDPRLKQRVLDIIDI
LFSDTVKARYIDKELSNRYVPRGNRRKVRAQLAIYDYIKSLEQPE

SEQ ID NO: 14 >gi|3452465|gb|AAC32883.1|
polyphosphate kinase [Vibrio cholerae]

MSADKLYIDKELSWLSFNERVLQEAADKTVPLIERIRFLGIFSNLL
DEFYKVRFADVKRQILINRERGGNDISKHLLSRMQSKALKLNQDFD
NLYNELILEMARRRIFLVNETQLDEIQLKWVKKYFHKVMLPHVTPI
MLRDDIDVMQFLKDEYAYIAVEMRSGDEFKYALIEIPTDQLPRFVM
LPEQKGKRRKTIILLDNIIRLCLDEIFRGFYDYDTLNGYAMKMTRD
AEYDLRHEVEYSLLEQMSEGLSQRLTALPVRFVYEREMPEAMLKFL

CYKLKISHYDSLIPGGRYHNFKDFISFPNVGRDYLENKPLPPMTCA

DFEGYANAFDAIRAQDILLHYPYHSFEHMTELVRQASFDPKVVSIK

INIYRVAKDSKLMNSLVDAVHNGKRVVVVVELQARFDEEANIEWSR

ILTDAGVHVIFGVPGMKIHAKLLLITRKEGDEFVRYAHIGTGNFHE

RTARIYTDFALLTANQELAAEVRAVFGYIENPFRPVKFNHLIVSPR

NSRTQIYRLLDSEIANAKAGKKAAITLKVNNLVDKGLINKLYGASA

AGVKIRMIIRGMCSLVPGVEGVSDNIEIISIIDRFLEHPRVLVVHN

DGNPQVFISSADWMERNIDHRIEVMAPIRDERLKQRIIDILNIQFI

DTVKARRIDKEMSNQYVERGNRRKVRSQIAIYDYLKNVEKQTRKAK

GQQETNDNSSQ

SEQ ID NO: 15 >gi|15600435|ref|NP_253929.1|
ppk gene product [Pseudomonas aeruginosa PAO1]

MNTQQGLDEIERIAADETVVANVESEAEVKMAETIPVETPPAVVPS

VDDSSLYIHRELSQLQFNIRVLEQALDESYPLLERLKFLLIFSSNL

DEFFEIRIAGLKKQITFAREQAGADGLLPHQALARISELVHEQVSR

QYRILNETLLPELAKHQIRFIRRRHWTLKIKTWVRRFFRDEIAPII

TPIGLDPTHPFPLLVNKSLNFIVELEGMDAFGRDSGLAIIPAPRLL

PRIIRLPEDVGGEGDNYVFLSSMIHAHADDLFPGMKVKGCYQFRLT

RNADLSVDTEDVEDLARALRGELFSRRYGDAVRLEVVDTCPQNLTN

YLLKQFGLSESELYKVSGPVNLTRLFSVTGLESHPELQYPPFTPAI

PRLLQKKENLFNVLSKLDVLLMHPFESFTPVIDLLRQAAKDPNVLA

IKQTLYRSGANSEIVDALVEAARNGKEVTAVIELRARFDEESNLQL

ASRLQQAGAVVIYGVVGFKTHAKMMLILRREDGELRRYAHLGTGNY

HAGNARLYTDYSLLTADVALCEDLHKLFNQLIGMGKTLRMKKLLHA

PFTLKKNLLEMINREAAQAALGQPAHIMAKVNSLTDPKVIRALYKA

SQAGVRIDLVVRGMCCLRPGIPGVSHNIHVRSIIGRFLEHSRIYYF

LNGGDEKLYLSSADWMERNLDMRVETCFPVEGKKLVQRVKKELETY

LTDNTQAWVLQADGSYQRLSPTGNQNPRNTQATLLEKLAAPVLTAR

SEQ ID NO: 16 >gi|30264066|ref|NP_846443.1|
ppk gene product [Bacillus anthracis str. Ames]

MELSKGNIVNLNDTAYYNNRELSWLAFNERVLQEAQDETNPLLERL

KFISIFSSNLDEFFMVRVAGLKDQVSAGFNQPENKAGLTPKKQLNK

IAIKAHELMTVQYGTFKNYVLPALELEGIERLTFHDLTKEQREFIE

EYFDEQIFPVLTPVAIDAYRPFPMLLNKSLNLATLLYDEKQVEEEN

RTKLGIVQVPSLLERFIFLPSEGQKHKFILLEDVISSFTHKLFTGY

KVSSVTRFRITRNADLTIHEEGARDLLKVIEKELKKRKWGAAVRLE

VGKEHIDERVLALLYEVLEVKDEDVYIMDGPLDLTCLFSLYKKLAP

LYEHLVYPALIPQRPQDLGDAEDVFEKAIEHDILLHHPFESFQPVV

DFVRDAADDPNVLAIKQTLYRVSGDSPIIQALKIAAEKGKQVTVLV

ELKARFDEENNVHWAKELEQAGCHVIYGVSHLKTHSKITLVVRRKN

GKIERFVHLGTGNYNDATAKLYTDFGYITSRKDFGVDATNFFNYLS

GYTTKPHFHHLSVAPFDIREQFMDLIDEEIRYHRQYGNGYIIAKMN

SLTDKPLIKKMYEASQAGVKVELIVRGTCCLRPGIPNVSENIRVVS

VVGRYLEHSRIYYFHHNGEEKIYLSSADWMTRNMEKRVEISFPILD

IEMKARIKAILQLTLADNVKTREQNKDGDYYYVINSGAEEIDSQVK

LFKMAYQNTDAE

TABLE 3

Polyphosphate kinase multiple alignment of SEQ ID NOs:
12 to 16 showing essential conserved residues which bind AMPPNP
(β-γ-imidoadenosine 5-phosphate, a nonhydrolysable ATP analogue)

| | | |
|---|---|---|
| gi\|13878615/1-675 | ---------------------------------------- | 0 |
| gi\|157157220/1-688 | ---------------------------------------- | 0 |
| gi\|3452465/1-701 | ---------------------------------------- | 0 |
| gi\|15600435/1-736 | MNTQQGLDEIERIAADETVVANVESEAEVKMAETIPVETP | 40 |
| gi\|30264066/1-702 | -----------------------------------MELS | 4 |
| | | |
| gi\|13878615/1-675 | ---------MNRFNELSWLAFNTRVINEAKDESLPLE | 31 |
| gi\|157157220/1-688 | ------MGQEKLIEKELSWLSFNERVLQEAADKSNPLE | 34 |
| gi\|3452465/1-701 | ------MSADKLIDELSWLSFNERVLQEAADKTVPLE | 34 |
| gi\|15600435/1-736 | PAVVPSVDDSSLIHRELSQLQFNIRVLEQALDESYPLE | 80 |
| gi\|30264066/1-702 | KGNIVNLNDTAYNNRELSWLAFNERVLQEAQDETNPLE | 44 |
| | | |
| gi\|13878615/1-675 | RLKEAIDTNLDEFMRVAGKQLYEHKIASKGID-GA | 70 |
| gi\|157157220/1-688 | RMERGISNNLDEFKVRFABKRRIIISEEQGSNS--- | 71 |
| gi\|3452465/1-701 | RIREGISNNLDEFKVRFADKRRQILINRERGGND--- | 71 |
| gi\|15600435/1-736 | RLEBLIESSNLDEFEIRIAGKQITFAREQAGAD-GL | 119 |
| gi\|30264066/1-702 | RLEISIESSNLDEFMRVAGKDQVSAGFNQPENKAGL | 84 |
| | | |
| gi\|13878615/1-675 | SPEEQLEIKHYLAHEIEERELE--FQKQALLFKKGCI | 108 |
| gi\|157157220/1-688 | HSRHLIQS-RVLKA-DQEFDGLYNELLEMARNQFL | 109 |
| gi\|3452465/1-701 | ISKHLSMQS-KALKL-NQDFDNLYNEILEMARRRFL | 109 |
| gi\|15600435/1-736 | LPHQALISE-LVHEQVSRQYRILNETLPELAKHQRF | 158 |
| gi\|30264066/1-702 | TPKKQLNKIAI-KAHELMTVQYGTFKNYLPALELEGER | 123 |

TABLE 3-continued

Polyphosphate kinase multiple alignment of SEQ ID NOs:
12 to 16 showing essential conserved residues which bind AMPPNP
(β-γ-imidoadenosine 5-phosphate, a nonhydrolysable ATP analogue)

```
gi|13878615/1-675    TPYNELNLEQKAKAKTI EKEQLYAL LEFK DSSHTFPPL       148
gi|157157220/1-688   INERQLSVNQQNWLRH FKQYLRQH TPIL NPDTDLVQF       149
gi|3452465/1-701     VNETQLDEIQLKWVKK SHKVMLPH TPIM RDDIDVMQF       149
gi|15600435/1-736    IRRRHWTLKIKTWVRR FRDEIAPI TEIG DPTHPFPLL       198
gi|30264066/1-702    LTFHDLTKEQREFIEE SDEQIFPV TPVA DAYRPFPML       163 gi|13878615/1-675    ANLTFALFARIKDKET----QIISY    KLPS-F FRF  E      183
gi|157157220/1-688   LKDDYTYLAV-----EIIRGDTIRY    EIPSDK PRF  N      184
gi|3452465/1-701     LKDEYAYIAV-----EMRSGDEFKY    EIPTDQ PRF  M      184
gi|15600435/1-736    VNKSLNFIVELEGMDAF--GRDSGL    PAPR-L PRI  R      235
gi|30264066/1-702    LNKSLNLATLLYDEKQVEEENRTKL    QVPS-L ERF  F      202 gi|13878615/1-675    L------EKGLF LAEEI EAHLEE LE---HEILDCMA         214
gi|157157220/1-688   LPPEAPRRRKPM LLDNI RYCLDD EKGFFDYDALNAYS        224
gi|3452465/1-701     LPEQKGKRRKTI LLDNI RLCLDE FRGFYDYDTLNGYA        224
gi|15600435/1-736    LPEDVGGEGDNY FLSSM HAHADD EPG---MKVKGCYQ        272
gi|30264066/1-702    LPSE--GQKHKF LLEDV SSFTHK ETG---YKVSSVTR        237 gi|13878615/1-675    F VTCDA IA TE EAHDYADLMSKS LRKRNQ EIVRLQT        254
gi|157157220/1-688   M MTRDA YD VH MEASLMELMSSS LKQRLT EPVRFVY        264
gi|3452465/1-701     M MTRDA YD RH VEYSLLEQMSEGL SQRLT LPVRFVY        264
gi|15600435/1-736    F LTRNA LS DT DVEDLARALRGEL FSRRY DAVRLEV        312
gi|30264066/1-702    F ITRNA LT HE GARDLLKVIEKEL KKRKW AAVRLEV        277 gi|13878615/1-675    -QKGSQELLKTI L ASLRSFQTHSYKKHK TGMHIYKSAIM      293
gi|157157220/1-688   -QRDMPNALVEV L----------REKLT SRYDSIVPGGR      293
gi|3452465/1-701     -EREMPEAMLKF L----------CYKLK SHYDSLIPGGR      293
gi|15600435/1-736    -VDTCPQNLTNY L----------LKQFG SESELYKVSGP      341
gi|30264066/1-702    GKEHIDERVLAL L----------YEVLE KDEDVYIMDGP      307 gi|13878615/1-675    L-NLGDLWELVNHSD--FKA KSPNFTPKIHPHFNE---N       327
gi|157157220/1-688   YHNFKDFINFPNVGK---AN VNKPLPRLRHIWFDKAQFR       330
gi|3452465/1-701     YHNFKDFISFPNVGR---DY ENKPLPPMTCADFEG--YA       328
gi|15600435/1-736    V-NLTRLFSVTGLES--HPE QYPPFTPAIPRLLQK--KE       376
gi|30264066/1-702    L-DLTCLFSLYKKLAPLYEH VYPALIPQRPQDLGD--AE       344 gi|13878615/1-675    DL KSIEKD LL FH ESE EPVI L EQA SDEAT   IK      367
gi|157157220/1-688   NG DAIRERD LL YY HTE EHVL L RQA FDESV   IK      370
gi|3452465/1-701     NA DAIRAQD LL HY HSF EHMT L RQA FDEKV   IK      368
gi|15600435/1-736    NL NVLSKLD LL MH ESE TPVI L RQA KDENV   IK      416
gi|30264066/1-702    DV EEKAIEHD LL HH ESE QPVV F RDA DDENV   IK      384 gi|13878615/1-675    M  YRV  KHSP VK LIE ASK-IQ VSV ELKARFDEES       406
gi|157157220/1-688   I  YRV  KDSR ID MIH AHNGKK VTV ELQARFDEEA       410
gi|3452465/1-701     I  YRV  KDSK MN LVDA VHNGKR VVV ELQARFDEEA       408
gi|15600435/1-736    Q  YRS  ANSE VD LVE ARNGKE VTA ELRARFDEES       456
gi|30264066/1-702    Q  YRV  GDSP IQ LKI AEKGKQ VTV ELKARFDEEN       424
                        **                                * gi|13878615/1-675    N HW KA ERA AL V  VFKL VH KML L T TDNQLR       446
gi|157157220/1-688   N HW KR  TEA VH V  APGL IH KLF L S ENGEVV       450
gi|3452465/1-701     N EW RI  TDA VH V  VPGM IH KLLL T EGDEFV       448
gi|15600435/1-736    N QL SR QQA AV V  VVGF TH KMM L EDGELR       496
gi|30264066/1-702    N HW KE EQA CH V  VSHL TH KITL V KNGKIE       464
                                              * gi|13878615/1-675       T   TGN NPLSA  YTDV FFS KNEIAN IIKL HS        486
gi|157157220/1-688      A   TGN NEKTA  YTDY LLT DARITN VRRV -N        489
gi|3452465/1-701        A   TGN HERTA  YTDF LLT NQELAA VRAV -G        487
gi|15600435/1-736       A   TGN HAGNA  YTDY LLT DVALCE LHKL -N        535
gi|30264066/1-702       V   TGN NDATA  TYDF YIT RKDFGV ATNF -N        503
                        * *     TGN      * * gi|13878615/1-675    L TSSATNSALET  PM KQI PKIIEL QN MNHQQEG-       525
gi|157157220/1-688   F ENPYRVTFDYL MV QNS RLLYEM DRE IANAQQGL       529
gi|3452465/1-701     Y ENPFRPVKFNH IV RNS TQIYRL DSE IANAKAGK       527
gi|15600435/1-736    Q IGMGKTLRMKK LH FTL KNLLEM NRE AQAALGQ       575
gi|30264066/1-702    Y SGYTTKPHFHH SV FDI EQFMDL DEE IRYHRQYG       543 gi|13878615/1-675    --Y ILKANA VDSE EWL QASQKGV DL RGICCL        563
gi|157157220/1-688   PSG TLKLNN VDKG DRL YASSSGVP NL RGMCSL        569
gi|3452465/1-701     KAA TLK VN TDKG NKL YGASAAGVK RM RGMCSL        567
gi|15600435/1-736    PAH MAKVNS TDPK RAL YKASQAGVR DL RGMCCL        615
gi|30264066/1-702    NGY IMKMNS TDKP KKM YEASQAGVK EL RGTCCL        583
                                                      *
```

TABLE 3-continued

Polyphosphate kinase multiple alignment of SEQ ID NOs:
12 to 16 showing essential conserved residues which bind AMPPNP
(β-γ-imidoadenosine 5-phosphate, a nonhydrolysable ATP analogue)

```
gi|13878615/1-675    K QXKG BNIRVYS  G  KEHAR YYFKH---EN   S    600
gi|157157220/1-688   I N EG DNIRAI  D  LEHDR YIFENGGDKK LS      609
gi|3452465/1-701     V G EG DNIEIIS D  LEHPR LVVHNDGNPQ  IS     607
gi|15600435/1-736    R G PG HNIHVRS G  LEHSR YYFLNGGDEK LS      655
gi|30264066/1-702    R G PN  BNIRVVS  G  LEHSR YYFHHNGEEK LS    623
                                           * gi|13878615/1-675    SADLMPRNL RR BLLI ATNPKIAH LHI EIQLK  L     640
gi|157157220/1-688   SADWMTRNI YR EVAT LLDPRLKQ LDI DILFS  V     649
gi|3452465/1-701     SADWMBRNI HR EVMA IRDERLKQ IDI NIQFI  V     647
gi|15600435/1-736    SADWMBRNL MR BTCF VEGKKLVQ KKE ETYLT  T     695
gi|30264066/1-702    SADWMTRNM KR EISF ILDIEMKA KAI QLTLA  V     663
                       *   *     * gi|13878615/1-675    KRYELNSKGRYIK  --SNPNDPLNS C----DYFEKQALKT  674
gi|157157220/1-688   KARYIDKELSNRY  -PRGNRRKVRA CLAIYDYIKSLEQPE  688
gi|3452465/1-701     KARRIDKEMSNQY  -ERGNRRKVRS CIAIYDYLKNVEKQT  686
gi|15600435/1-736    QAWVLQADGSYQR  SPTGNQNPRNT CATLLEKLAAPVLTA  735
gi|30264066/1-702    KTREQNKDGDYYY  INSGAEE-IDS CVKLFKMAYQNTDAE  702 gi|13878615/1-675    F---------------                            675
gi|157157220/1-688   ----------------                            688
gi|3452465/1-701     RKAKGQQETNDNSSQ                             701
gi|15600435/1-736    R---------------                            736
gi|30264066/1-702    ----------------                            702
```

^ indicates conserved residues involved in side-chain contacts with the adenine ring of the AMPPNP,
* indicates residues involved in side-chain contacts with the phosphate groups of AMPPNP.
Based on Zhu, Y., W. Huang, S. S. Lee, and W. Xu, *Crystal structure of a polyphosphate kinase and its implications for polyphosphate synthesis.* EMBO Rep, 2005. 6(7): p. 681-7.). PPK1 cds from GI:13878615 *Helicobacter pylori*, GI:157157220 *Escherichia coli*, GI:3452465 *Vibrio cholerae*, GI:15600435 *Pseudomonas aeruginosa*, GI:30264066 *Bacillus anthracis*.

The ligation product was transformed into *E. coli* Top 10 electrocompetent cells (Invitrogen) by electroporation. The new vector, named pET23bpduP18-ppk, was extracted and the ppk insert was sequenced (GATC-Biotech) to confirm no mutation had occurred. Two constructs, pET23bpduP18-ppk and pSF37 (pLysS-pduABJKNU, expressing an empty pdu microcompartment), were co-transferred into *E. coli* BL21 (DE3) by electroporation.

Polyphosphate extraction from pelleted *E. coli* cells was carried out using a GENECLEAN™ kit (MP Biomedicals Europe) as described (Ault-Riche, D., C. D. Fraley, C.- M. Tzeng, and A. Kornberg, *Novel Assay Reveals Multiple Pathways Regulating Stress-Induced Accumulations of Inorganic Polyphosphate in Escherichia coli.* J. Bacteriol., 1998. 180 (7): p. 1841-1847). Briefly, 4 M guanidine isothiocyanate (GITC)-50 mM Tris-HCl, pH 7 (GITC lysis buffer), prewarmed to 95° C. was used to lyse pelleted cells, then 10% sodium dodecyl sulphate (SDS), 95% ethanol, and Glassmilk was added to adsorb polyphosphate, washing with New Wash buffer. Polyphosphate was eluted from the pellet by adding 50 µl of 50 mM Tris-HCl (pH 8.0) at 95° C. for 2 min, recovery of polyphosphate was completed with two additional elutions.

Molar quantification of phosphate as polyphosphate in cell extracts was performed metachromatically using the 530/630 nm absorbance ratio of 10 µl of sample added to 1 ml of toluidine dye solution (6 mg/L toluidine blue in 40 mM acetic acid) as described (Mullan, A., J. P. Quinn, and J. W. McGrath, *A nonradioactive method for the assay of polyphosphate kinase activity and its application in the study of polyphosphate metabolism in Burkholderia cepacia.* Analytical Biochemistry, 2002. 308(2): p. 294-299). A polyphosphate standard curve was prepared using sodium phosphate glass Type 45 (S4379 Aldrich) and sodium hexametaphosphate (SX0583). Protein concentration of cell extracts was measured using 10-µl sample, with Coomassie Plus Protein Assay Reagent (Pierce) with bovine serum albumin as the standard, resuspended in the same buffer as the sample. Phosphate uptake was determined as follows. Overnight cultures of bacteria were induced by 0.5 mM IPTG in Luria broth for 1 hr before transfer to pH 5.5 MOPS medium containing 0.01 mM $FeSO_4 \cdot 7H_2O$ and 0.5 mM potassium phosphate, at an optical density of 600 nm (OD600) of 0.2. Incubation was continued at 37° C. with intermittent sampling of 0.2 ml up to 48 hours. Samples were centrifuged and supernatant used for phosphate assay, and the pellet used for polyphosphate and protein assays. Phosphate was assayed using a molybdovanadate colorimetric method (Eaton, A., L. Clesceri, E. Rice, A. Greenberg, and M. Franson, eds. *Standard Methods for the Examination of Water and Wastewater.* 21st ed. 2005, American Public Health Association). 0.2 ml of molybdovanadate solution (Reagecon) was added to 5 ml of culture supernatant, mixed and incubated at room temperature for 5 minutes. Optical density of 1 ml at 430 nm was measured against a blank of 4% molybdovanadate in distilled water and a calibration curve of potassium phosphate in MOPS.

Polyphosphate was visualised in polyacrylamide gels by 4'6-diamidino-2-phenylindol (DAPI) negative staining. Gels were agitated for 30 min in 2 mg/mL DAPI in fixative at room temperature. Gels were then exposed to 365 nm light via a UV transilluminator for 2-20 min to induce specific photobleaching of polyphosphate bound to DAPI.

Microscopy

Fluorescent microscopy visualisation of intracellular polyphosphate with tetracycline staining was carried out as described (Smith, S. A. and J. H. Morrissey, *Sensitive fluorescence detection of polyphosphate in polyacrylamide gels using 4',6-diamidino-2-phenylindol.* Electrophoresis, 2007.

28(19): p. 3461-3465). A 2-mg ml$^{-1}$ stock solution of tetracycline hydrochoride (Sigma) in double-distilled water was added to cell suspensions to give a final concentration of 0.225 mM. Fresh stock solutions were prepared before each experiment because of rapid deterioration in fluorescence with solution storage. Microscopy was carried out with an Olympus BX51 microscope excitation G 365, BS 395, emission LP 420 for green fluorescence. Polyphosphate granules were also visualised in fixed films by Neisser's stain using Chrysoidin counterstain.

For cryo-electron microscopy (TEM) (FIG. 5) a single colony was inoculated in LB medium with 30 μg/ml chloramphenicol and 100 μg/ml ampicillin, and grown with shaking at 37° C. for about 16 hrs. 1 ml of overnight culture was inoculated in 50 ml fresh LB medium containing the same antibiotics and grown for about 2-3 hrs until OD600 reaches 0.4. 0.2 mM IPTG was added to the culture and bacterium were grown for another 1 hrs. Cells were then harvested by centrifugation and washed twice with MOPS medium without added $K_2HPO_4$. The washed cells were resuspended in 50 ml of MOPS medium containing 1 mM $K_2HPO_4$, 30 μg/ml chloramphenicol, 100 μg/ml ampicillin, 0.2 mM IPTG and 30 μg/ml of cefsulodin and incubated at 37° C. for between 4 and 18 hours. Bacterial cell cultures of OD600 of 0.5 were used neat for microscopy, cultures less than OD600 0.5 were concentrated by centrifugation at 12,000 rpm for 2 minutes with resuspension of deposit in MOPS to achieve OD600 of 0.5.

100 μl of 10 nm colloidal gold was mixed with 25 μl of 5% BSA and centrifuged at 12,000×g for 15 minutes. Supernatant was removed and pellet of colloidal gold was mixed with 20 μl of cells at appropriate density (OD600=0.5). 300 mesh quantifoil grids were glow discharged for 3 minutes. 4 μl of sample was added to the carbon side of a grid in a Vitrobot at 95% RH, 21 C. Blotting was performed automatically with a Vitrobot with two 1 second blots and 1 second dry time before plunging into liquid ethane. Grid was transferred under liquid nitrogen for imaging. Imaging was performed on a Technai Polara G2 at 300 keV under cryo-conditions. All tomograms were collected using SerialEM on a 4K GATAN CCD binned at 2K×2K resolution.

In this specification, the term "system" should be taken to include, but not limited to, a "biological system", for example a cell, a cell line, a tissue sample, an organ, a unicellular or multicellular organism, or a lower or higher life form; a "water body" or "body of water", for example a lake, a reservoir, a pond, a swimming pool, a canal, settlement ponds/pools, water treatment tanks, domestic water storage containers, rivers, streams, an aquarium, and the like; and "waste streams", for example water treatment tanks, agricultural run-off treatment tanks, and the like.

When the "system" is a human or animal body, various delivery methods are known and can be used to administer a therapeutic of the invention, e.g., encapsulation in liposomes, microparticles, microcapsules.

Methods of introduction include but are not limited to intradermal, intramuscular, intraperitoneal, intravenous, subcutaneous, intranasal, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents and dietary supplements. Administration can be systemic or local. Pulmonary administration can also be employed, e.g., by use of an inhaler or nebulizer, and formulation with an aerosolizing agent.

It may be desirable to administer the compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

The present invention also provides pharmaceutical compositions. Such compositions comprise a therapeutically effective amount of a therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

Yoghurt or soy yoghurt can also be used to administer the recombinant bacteria of the present invention. The recombinant bacteria are preferably probiotic bacteria or bacteria suitable for human consumption, for example, lactic acid bacteria (selected from, but not limited to, *Lactobacillus*, (*L. reuteri. L. acidophilus, L. casei, L. plantarum, L. johnsonii, L. rhamnosus*), *Lactococcus lactis*, *Bifidobacteria* (*B. infantis, B. breve, B. longum, Bifidobacterium animalis* ssp. *Lactis*), *Enterococcus faecalis, E. faecium*), *Streptoccus thermophilus*, and *Escherichia coli* strains. Yeast, such as Saccharomyces, may also be used to express and deliver the microcompartment and PPK enzyme to an animal or human body in a probiotic formulation.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In the specification, the expression "low molecular weight substrate" should be understood to mean a substrate which is sufficiently small to pass into the microcompartment from the bacterial cytoplasm through the pores of the microcompartment.

In the specification, the expression "polymeric" or "high molecular weight molecular product(s)" should be understood to mean products of a size that is too large to pass out of the microcompartment through the pores of the microcompartment.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

SEQUENCE LISTING

```
<160> NUMBER OF SEQ ID NOS: 16

<210> SEQ ID NO 1
<211> LENGTH: 45
<212> TYPE: DNA
<213> ORGANISM: Artificial Organism
<220> FEATURE:
<223> OTHER INFORMATION: Forward Primer

<400> SEQUENCE: 1
agtgagctca tgggtcagga aaagctatac atcgaaaaag aactc              45

<210> SEQ ID NO 2
<211> LENGTH: 28
<212> TYPE: DNA
<213> ORGANISM: Artificial Sequence
<220> FEATURE:
<223> OTHER INFORMATION: Reverse Primer

<400> SEQUENCE: 2
aataaagctt ttattcaggt tgttcgag                                 28

<210> SEQ ID NO 3
<211> LENGTH: 2074
<212> TYPE: DNA
<213> ORGANISM: Escherichia coli

<400> SEQUENCE: 3
atgggtcagg aaaagctata catcgaaaaa gaactcagtt ggttatcgtt caatgaacgc    60
gtgcttcagg aagcggcgga caaatctaac ccgctgattg aaaggatgcg tttcctgggg   120
atctattcca ataaccttga tgagttctat aaagtccgct tcgctgaact gaagcgacgc   180
atcattatta gcgaagaaca aggctccaac tctcattccc gccatttact gggcaaaatt   240
cagtcccggg tgctgaaagc cgatcaggaa ttcgacggcc tctacaacga gctattgctg   300
gagatggcgc gcaaccagat cttcctgatt aatgaacgcc agctctccgt caatcaacaa   360
aactggctgc gtcattattt taagcagtat ctgcgtcagc acattacgcc gattttaatc   420
aatcctgaca ctgacttagt gcagttcctg aaagatgatt acacctatct ggcggtggaa   480
attatccgtg gcgataccat ccgttacgcg ctgctggaga tcccatcaga taaagtgccg   540
cgctttgtga atttaccgcc agaagcgccg cgtcgacgca agccgatgat tcttctggat   600
aacattctgc gttactgcct tgatgatatt ttcaaaggct tctttgatta tgacgcgctg   660
aatgcctatt caatgaagat gacccgcgat gccgaatacg atttagtgca tgagatggaa   720
gccagcctga tggagttgat gtcttccagt ctcaagcagc gtttaactgc tgagccggtg   780
cgttttgttt atcagcgcga tatgcccaat gcgctggttg aagtgttacg cgaaaaactg   840
actatttccc gctacgactc catcgtcccc ggcggtcgtt atcataattt taaagacttt   900
attaatttcc ccaatgtcgg caaagccaat ctggtgaaca aaccactgcc gcgtttacgc   960
catatttggt ttgataaagc ccagttccgc aatggttttg atgccattcg cgaacgcgat  1020
gtgttgctct attatcctta tcacaccttt gagcatgtgc tggaactgct gcgtcaggct  1080
```

```
tcgttcgacc cgagcgtact ggcgattaaa attaacattt accgcgtggc gaaagattca      1140
cgcatcatcg actcgatgat ccacgccgca cataacggta agaaagtcac cgtggtggtt      1200
gagttacagg cgcgtttcga cgaagaagcc aacattcact gggcgaagcg cctgaccgaa      1260
gcaggcgtgc acgttatctt ctctgcgccg gggctgaaaa ttcacgccaa actgttcctg      1320
atttcacgta agaaaacgg tgaagtggtg cgttatgcac acatcgggac cgggaacttt       1380
aacgaaaaaa ccgcgcgtct ttatactgac tattcgttgc tgaccgccga tgcgcgcatc      1440
accaacgaag tacggcgggt atttaacttt attgaaaacc cataccgtcc ggtgacattt      1500
gattatttaa tggtatcgcc gcaaaactcc cgccgcctat tgtatgaaat ggtggaccgc      1560
gagatcgcca acgcgcagca agggctgccc agtggtatca ccctgaagct aaataacctt      1620
gtcgataaag gcctggttga tcgtctgtat gcggcctcca gctccggcgt accggttaat      1680
ctgctggttc gcggaatgtg ttcgctgatc cccaatctgg aaggcattag cgacaacatt      1740
cgtgccatca gtattgttga ccgttacctt gaacatgacc gggtttatat ttttgaaaat      1800
ggcggcgata aaaaggtcta cctttcttcc gccgactgga tgacgcgcaa tattgattat      1860
cgtattgaag tggcgacgcc gctgctcgat ccgcgcctga agcagcgggt actgacatc       1920 atcgacatat tgttcagcga tacggtcaaa gcacgttata tcgataaaga actcagtaat      1980
cgctacgttc cccgcggcaa tcgccgcaaa gtacgggcgc agttggcgat ttatgactac      2040
atcaaatcac tcgaacaacc tgaataaaag cttg                                  2074
```

<210> SEQ ID NO 4
<211> LENGTH: 19
<212> TYPE: PRT
<213> ORGANISM: Escherichia coli

<400> SEQUENCE: 4

Met Asn Thr Ser Glu Leu Glu Thr Leu Ile Arg Asn Ile Leu Ser Glu
1               5                   10                  15

Gln Leu Ala

<210> SEQ ID NO 5
<211> LENGTH: 93
<212> TYPE: PRT
<213> ORGANISM: Citrobacter freundii

<400> SEQUENCE: 5

Met Gln Gln Glu Ala Leu Gly Met Val Glu Thr Lys Gly Leu Thr Ala
1               5                   10                  15

Ala Ile Glu Ala Ala Asp Ala Met Val Lys Ser Ala Asn Val Met Leu
            20                  25                  30

Val Gly Tyr Glu Lys Ile Gly Ser Gly Leu Val Thr Val Ile Val Arg
        35                  40                  45

Gly Asp Val Gly Ala Val Lys Ala Ala Thr Asp Ala Gly Ala Ala Ala
    50                  55                  60

Ala Arg Asn Val Gly Glu Val Lys Ala Val His Val Ile Pro Arg Pro
65                  70                  75                  80

His Thr Asp Val Glu Lys Ile Leu Pro Lys Gly Ile Ser
                85                  90

<210> SEQ ID NO 6
<211> LENGTH: 270
<212> TYPE: PRT
<213> ORGANISM: Citrobacter freundii

<400> SEQUENCE: 6

```
Met Ser Ser Asn Glu Leu Val Asp Gln Ile Met Ala Gln Val Ile Ala
1               5                   10                  15

Arg Val Ala Thr Pro Glu Gln Gln Ala Ile Pro Glu Asn Asn Pro Pro
            20                  25                  30

Thr Arg Glu Thr Ala Met Ala Glu Lys Ser Cys Ser Leu Thr Glu Phe
        35                  40                  45

Val Gly Thr Ala Ile Gly Asp Thr Val Gly Leu Val Ile Ala Asn Val
    50                  55                  60

Asp Ser Ala Leu Leu Asp Ala Met Lys Leu Glu Lys Arg Tyr Arg Ser
65              70                  75                  80

Ile Gly Ile Leu Gly Ala Arg Thr Gly Ala Gly Pro His Ile Met Ala
                85                  90                  95

Ala Asp Glu Ala Val Lys Ala Thr Asn Thr Glu Val Val Ser Ile Glu
            100                 105                 110

Leu Pro Arg Asp Thr Lys Gly Gly Ala Gly His Gly Ser Leu Ile Ile
        115                 120                 125

Leu Gly Gly Asn Asp Val Ser Asp Val Lys Arg Gly Ile Glu Val Ala
130                 135                 140

Leu Lys Glu Leu Asp Arg Thr Phe Gly Asp Val Tyr Ala Asn Glu Ala
145                 150                 155                 160

Gly His Ile Glu Met Gln Tyr Thr Ala Arg Ala Ser Tyr Ala Leu Glu
                165                 170                 175

Lys Ala Phe Gly Ala Pro Ile Gly Arg Ala Cys Gly Val Ile Val Gly
            180                 185                 190

Ala Pro Ala Ser Val Gly Val Leu Met Ala Asp Thr Ala Leu Lys Ser
        195                 200                 205

Ala Asn Val Glu Val Val Ala Tyr Ser Ser Pro Ala His Gly Thr Ser
210                 215                 220

Phe Ser Asn Glu Ala Ile Leu Val Ile Ser Gly Asp Ser Gly Ala Val
225                 230                 235                 240

Arg Gln Ala Val Ile Ser Ala Arg Glu Ile Gly Lys Thr Val Leu Gly
                245                 250                 255

Thr Leu Gly Ser Glu Pro Lys Asn Asp Arg Pro Ser Tyr Ile
            260                 265                 270
```

<210> SEQ ID NO 7
<211> LENGTH: 91
<212> TYPE: PRT
<213> ORGANISM: Citrobacter freundii

<400> SEQUENCE: 7

```
Met Asn Asn Ala Leu Gly Leu Val Glu Thr Lys Gly Leu Val Gly Ala
1               5                   10                  15

Ile Glu Ala Ala Asp Ala Met Val Lys Ser Ala Asn Val Gln Leu Val
            20                  25                  30

Gly Tyr Glu Lys Ile Gly Ser Gly Leu Ile Thr Val Met Val Arg Gly
        35                  40                  45

Asp Val Gly Ala Val Lys Ala Ala Val Asp Ala Gly Ser Ala Ala Ala
    50                  55                  60

Ser Ala Val Gly Glu Val Lys Ser Cys His Val Ile Pro Arg Pro His
65              70                  75                  80

Ser Asp Val Glu Ala Ile Leu Pro Lys Ser Ala
                85                  90
```

<210> SEQ ID NO 8
<211> LENGTH: 156
<212> TYPE: PRT
<213> ORGANISM: Citrobacter freundii

<400> SEQUENCE: 8

Met Lys Gln Ser Leu Gly Leu Leu Glu Val Ser Gly Leu Ala Leu Ala
1               5                   10                  15

Ile Ser Cys Ala Asp Val Met Ala Lys Ala Ala Ser Ile Thr Leu Val
            20                  25                  30

Gly Leu Glu Lys Thr Asn Gly Ser Gly Trp Met Val Ile Lys Ile Ile
        35                  40                  45

Gly Asp Val Ala Ser Val Gln Ala Ala Ile Ser Thr Gly Val Ser Phe
    50                  55                  60

Ala Asp Gln Arg Asp Gly Leu Val Ala His Lys Val Ile Ser Arg Pro
65                  70                  75                  80

Gly Asp Gly Ile Leu Ser His Ser Val Thr Pro Glu Ser Glu Ser Glu
                85                  90                  95

Pro Ala Pro Ala Pro Thr Pro Val Val Pro His Glu Glu Ile Pro Glu
            100                 105                 110

Asp His Ala Ala Pro Glu Ala Pro Gln Asp Ala Glu Leu Ile Ser Cys
        115                 120                 125

Asn Leu Cys Leu Asp Pro Ala Cys Pro Arg Gln Lys Gly Glu Pro Arg
    130                 135                 140

Ser Leu Cys Leu His Ser Gly Lys Arg Gly Glu Ala
145                 150                 155

<210> SEQ ID NO 9
<211> LENGTH: 91
<212> TYPE: PRT
<213> ORGANISM: Citrobacter freundii

<400> SEQUENCE: 9

Met His Leu Ala Arg Val Thr Gly Val Val Ser Thr Gln Lys Ser
1               5                   10                  15

Pro Ser Leu Val Gly Lys Lys Leu Leu Leu Val Arg Arg Val Ser Ala
            20                  25                  30

Asp Gly Glu Leu Pro Ala Ser Pro Val Ser Gly Asp Glu Val Ala Val
        35                  40                  45

Asp Ser Val Gly Ala Gly Thr Gly Glu Leu Val Leu Leu Ser Ser Gly
    50                  55                  60

Ser Ser Ala Arg His Val Phe Ser Gly Pro Asn Glu Ala Ile Asp Leu
65                  70                  75                  80

Ala Ile Val Gly Ile Val Asp Thr Leu Ser Arg
                85                  90

<210> SEQ ID NO 10
<211> LENGTH: 116
<212> TYPE: PRT
<213> ORGANISM: Citrobacter freundii

<400> SEQUENCE: 10

Met Glu Arg Gln Pro Thr Thr Asp Arg Met Ile Gln Glu Tyr Val Pro
1               5                   10                  15

Gly Lys Gln Val Thr Leu Ala His Leu Ile Ala Asn Pro Gly Lys Asp
            20                  25                  30

```
Leu Phe Lys Lys Leu Gly Leu Pro Glu Ser Val Ser Ala Ile Gly Ile
             35                  40                  45

Leu Thr Ile Thr Pro Ser Glu Ala Ser Ile Ile Ala Cys Asp Ile Ala
 50                  55                  60

Thr Lys Ser Gly Ala Val Glu Ile Gly Phe Leu Asp Arg Phe Thr Gly
 65                  70                  75                  80

Ala Val Val Leu Thr Gly Asp Val Ser Ala Val Glu Tyr Ala Leu Lys
                 85                  90                  95

Gln Val Thr Arg Thr Leu Gly Glu Met Met Arg Phe Thr Ala Cys Pro
            100                 105                 110

Ile Thr Arg Thr
            115

<210> SEQ ID NO 11
<211> LENGTH: 874
<212> TYPE: PRT
<213> ORGANISM: Geminocystis herdmanii (Synechocystis sp) strain PCC6308

<400> SEQUENCE: 11

Met Lys Ile Leu Lys Thr Gln Thr Leu Arg Gly Pro Asn Tyr Trp Ser
 1               5                  10                  15

Ile Arg Arg Gln Lys Leu Ile Gln Met Arg Leu Asp Leu Glu Asp Val
                20                  25                  30

Ala Glu Lys Pro Ser Asn Leu Ile Pro Gly Phe Tyr Glu Gly Leu Val
             35                  40                  45

Lys Ile Leu Pro Ser Leu Val Glu His Phe Cys Ser Arg Asp His Arg
 50                  55                  60

Gly Gly Phe Leu Glu Arg Val Gln Glu Gly Thr Tyr Met Gly His Ile
 65                  70                  75                  80

Val Glu His Ile Ala Leu Glu Leu Gln Glu Leu Ala Gly Met Pro Val
                 85                  90                  95

Gly Phe Gly Arg Thr Arg Glu Thr Ser Thr Pro Gly Ile Tyr Asn Val
            100                 105                 110

Val Phe Glu Tyr Val Tyr Glu Glu Ala Gly Arg Tyr Ala Gly Arg Val
            115                 120                 125

Ala Val Arg Leu Cys Asn Ser Ile Ile Thr Thr Gly Ala Tyr Gly Leu
        130                 135                 140

Asp Glu Leu Ala Gln Asp Leu Ser Asp Leu Lys Asp Leu Arg Ala Asn
145                 150                 155                 160

Ser Ala Leu Gly Pro Ser Thr Glu Thr Ile Ile Lys Glu Ala Glu Ala
                165                 170                 175

Arg Gln Ile Pro Trp Met Leu Leu Ser Ala Arg Ala Met Val Gln Leu
            180                 185                 190

Gly Tyr Gly Ala Asn Gln Gln Arg Ile Gln Ala Thr Leu Ser Asn Lys
        195                 200                 205

Thr Gly Ile Leu Gly Val Glu Leu Ala Cys Asp Lys Glu Gly Thr Lys
    210                 215                 220

Thr Thr Leu Ala Glu Ala Gly Ile Pro Val Pro Arg Gly Thr Val Ile
225                 230                 235                 240

Tyr Tyr Ala Asp Glu Leu Ala Asp Ala Ile Ala Asp Val Gly Gly Tyr
                245                 250                 255

Pro Ile Val Leu Lys Pro Leu Asp Gly Asn His Gly Arg Gly Ile Thr
            260                 265                 270

Ile Asp Ile Asn Ser Gln Gln Glu Ala Glu Glu Ala Tyr Asp Leu Ala
        275                 280                 285
```

-continued

```
Ser Ala Ala Ser Lys Thr Arg Ser Val Ile Val Glu Arg Tyr Tyr Lys
        290                 295                 300

Gly Asn Asp His Arg Val Leu Val Ile Asn Gly Lys Leu Val Ala Val
305                 310                 315                 320

Ser Glu Arg Ile Pro Ala His Val Thr Gly Asn Gly Ser Ser Thr Ile
                325                 330                 335

Glu Glu Leu Ile Gln Glu Thr Asn Glu His Pro Asp Arg Gly Asp Gly
                340                 345                 350

His Asp Asn Val Leu Thr Arg Ile Ser Ile Asp Arg Thr Ser Leu Gly
            355                 360                 365

Val Leu Lys Arg Gln Gly Phe Glu Met Asp Thr Val Leu Lys Lys Gly
370                 375                 380

Glu Val Ala Tyr Leu Arg Ala Thr Ala Asn Leu Ser Thr Gly Gly Ile
385                 390                 395                 400

Ala Ile Asp Arg Thr Asp Glu Ile His Pro Gln Asn Ile Trp Ile Ala
                405                 410                 415

Glu Arg Val Ala Lys Ile Ile Gly Leu Asp Ile Ala Gly Ile Asp Val
                420                 425                 430

Val Thr Pro Asp Ile Thr Lys Pro Leu Thr Glu Val Asp Gly Val Ile
            435                 440                 445

Val Glu Val Asn Ala Ala Pro Gly Phe Arg Met His Val Ala Pro Ser
450                 455                 460

Gln Gly Leu Pro Arg Asn Val Ala Ala Pro Val Ile Asp Met Leu Phe
465                 470                 475                 480

Pro Asp Asn His Pro Ser Arg Ile Pro Ile Leu Ala Val Thr Gly Thr
                485                 490                 495

Asn Gly Lys Thr Thr Thr Thr Arg Leu Leu Ala His Ile Tyr Arg Gln
                500                 505                 510

Thr Gly Lys Val Val Gly Tyr Thr Ser Thr Asp Gly Ile Tyr Leu Gly
            515                 520                 525

Asp Tyr Met Val Glu Lys Gly Asp Asn Thr Gly Pro Val Ser Ala Gly
            530                 535                 540

Val Ile Leu Arg Asp Pro Thr Val Glu Val Ala Val Leu Glu Cys Ala
545                 550                 555                 560

Arg Gly Gly Ile Leu Arg Ser Gly Leu Ala Phe Glu Ser Cys Asp Val
                565                 570                 575

Gly Val Val Leu Asn Val Ala Glu Asp His Leu Gly Leu Gly Asp Ile
                580                 585                 590

Asp Thr Ile Glu Gln Met Ala Lys Val Lys Gly Val Ile Ala Glu Ser
            595                 600                 605

Val Asn Ala Asp Gly Tyr Ala Val Leu Asn Ala Asp Asp Pro Leu Val
610                 615                 620

Ala Gln Met Ala Lys Asn Val Lys Gly Lys Ile Ala Tyr Phe Ser Met
625                 630                 635                 640

Ser Lys Asp Asn Pro Ile Ile Ile Asp His Leu Arg Arg Asn Gly Met
                645                 650                 655

Ala Ala Val Tyr Glu Asn Gly Tyr Leu Ser Ile Phe Glu Gly Glu Trp
                660                 665                 670

Thr Leu Arg Ile Glu Lys Ala Glu Asn Ile Pro Val Thr Met Lys Ala
            675                 680                 685

Met Ala Pro Phe Met Ile Ala Asn Ala Leu Ala Ala Ser Leu Ala Ala
690                 695                 700
```

```
Phe Val His Gly Ile Asp Ile Glu Leu Ile Arg Gln Gly Val Arg Ser
705                 710                 715                 720

Phe Asn Pro Gly Ala Asn Gln Thr Pro Gly Arg Met Asn Leu Phe Asp
            725                 730                 735

Met Lys Asp Phe Ser Val Leu Ile Asp Tyr Ala His Asn Pro Ala Gly
        740                 745                 750

Tyr Leu Ala Val Gly Ser Phe Val Lys Asn Trp Lys Gly Asp Arg Leu
    755                 760                 765

Gly Val Ile Gly Gly Pro Asp Arg Arg Asp Glu Asp Leu Met Leu
770                 775                 780

Leu Gly Lys Ile Ala Ser Gln Ile Phe Asp His Ile Ile Lys Glu
785                 790                 795                 800

Asp Asp Asp Asn Arg Gly Arg Asp Arg Gly Thr Val Ala Asp Leu Ile
                805                 810                 815

Ala Lys Gly Ile Val Ala Glu Asn Pro Asn Ala Ser Tyr Asp Asp Ile
            820                 825                 830

Leu Asp Glu Thr Glu Ala Ile Glu Thr Gly Leu Lys Lys Val Asp Lys
        835                 840                 845

Gly Gly Leu Val Val Ile Phe Pro Glu Ser Val Thr Gly Ser Ile Glu
850                 855                 860

Met Ile Glu Lys Tyr His Leu Ser Ser Glu
865                 870

<210> SEQ ID NO 12
<211> LENGTH: 675
<212> TYPE: PRT
<213> ORGANISM: Helicobacter pylori 26695

<400> SEQUENCE: 12

Met Asn Arg Phe Phe Asn Arg Glu Leu Ser Trp Leu Ala Phe Asn Thr
1               5                   10                  15

Arg Val Leu Asn Glu Ala Lys Asp Glu Ser Leu Pro Leu Leu Glu Arg
            20                  25                  30

Leu Lys Phe Leu Ala Ile Tyr Asp Thr Asn Leu Asp Glu Phe Tyr Met
        35                  40                  45

Ile Arg Val Ala Gly Leu Lys Gln Leu Tyr Glu His Lys Ile Ala Ser
50                  55                  60

Lys Gly Ile Asp Gly Ala Ser Pro Glu Glu Gln Leu Glu Lys Ile Lys
65                  70                  75                  80

His Tyr Leu Ala His Glu Ile Glu Glu Arg Glu Leu Glu Phe Gln Lys
                85                  90                  95

Ile Gln Ala Leu Leu Phe Lys Lys Gly Leu Cys Ile Thr Pro Tyr Asn
            100                 105                 110

Glu Leu Asn Leu Glu Gln Lys Ala Lys Ala Lys Thr Tyr Phe Lys Glu
        115                 120                 125

Gln Leu Tyr Ala Leu Val Leu Pro Phe Lys Leu Asp Ser Ser His Thr
    130                 135                 140

Phe Pro Pro Leu Ala Asn Leu Thr Phe Ala Leu Phe Ala Arg Ile Lys
145                 150                 155                 160

Asp Lys Glu Thr Gln Ile Ile Ser Tyr Ala Leu Ile Lys Leu Pro Ser
                165                 170                 175

Phe Ile Phe Arg Phe Val Glu Leu Glu Lys Gly Leu Phe Val Leu Ala
            180                 185                 190

Glu Glu Ile Val Glu Ala His Leu Glu Glu Leu Phe Leu Glu His Glu
        195                 200                 205
```

```
Ile Leu Asp Cys Met Ala Phe Arg Val Thr Cys Asp Ala Asp Ile Ala
    210                 215                 220
Ile Thr Glu Asp Glu Ala His Asp Tyr Ala Asp Leu Met Ser Lys Ser
225                 230                 235                 240
Leu Arg Lys Arg Asn Gln Gly Glu Ile Val Arg Leu Gln Thr Gln Lys
                245                 250                 255
Gly Ser Gln Glu Leu Leu Lys Thr Leu Leu Ala Ser Leu Arg Ser Phe
            260                 265                 270
Gln Thr His Ser Tyr Lys Lys His Lys Leu Thr Gly Met His Ile Tyr
        275                 280                 285
Lys Ser Ala Ile Met Leu Asn Leu Gly Asp Leu Trp Glu Leu Val Asn
    290                 295                 300
His Ser Asp Phe Lys Ala Leu Lys Ser Pro Asn Phe Thr Pro Lys Ile
305                 310                 315                 320
His Pro His Phe Asn Glu Asn Asp Leu Phe Lys Ser Ile Glu Lys Gln
                325                 330                 335
Asp Leu Leu Phe His Pro Tyr Glu Ser Phe Glu Pro Val Ile Asp
            340                 345                 350
Leu Ile Glu Gln Ala Ala Ser Asp Pro Ala Thr Leu Ser Ile Lys Met
    355                 360                 365
Thr Leu Tyr Arg Val Gly Lys His Ser Pro Ile Val Lys Ala Leu Ile
    370                 375                 380
Glu Ala Ala Ser Lys Ile Gln Val Ser Val Leu Val Glu Leu Lys Ala
385                 390                 395                 400
Arg Phe Asp Glu Glu Ser Asn Leu His Trp Ala Lys Ala Leu Glu Arg
                405                 410                 415
Ala Gly Ala Leu Val Val Tyr Gly Val Phe Lys Leu Lys Val His Ala
            420                 425                 430
Lys Met Leu Leu Ile Thr Lys Lys Thr Asp Asn Gln Leu Arg His Phe
    435                 440                 445
Thr His Leu Ser Thr Gly Asn Tyr Asn Pro Leu Ser Ala Lys Val Tyr
    450                 455                 460
Thr Asp Val Ser Phe Phe Ser Ala Lys Asn Glu Ile Ala Asn Asp Ile
465                 470                 475                 480
Ile Lys Leu Phe His Ser Leu Leu Thr Ser Ser Ala Thr Asn Ser Ala
                485                 490                 495
Leu Glu Thr Leu Phe Met Ala Pro Lys Gln Ile Lys Pro Lys Ile Ile
            500                 505                 510
Glu Leu Ile Gln Asn Glu Met Asn His Gln Gln Glu Gly Tyr Ile Ile
    515                 520                 525
Leu Lys Ala Asn Ala Leu Val Asp Ser Glu Ile Glu Trp Leu Tyr
    530                 535                 540
Gln Ala Ser Gln Lys Gly Val Lys Ile Asp Leu Ile Ile Arg Gly Ile
545                 550                 555                 560
Cys Cys Leu Lys Pro Gln Val Lys Gly Leu Ser Glu Asn Ile Arg Val
                565                 570                 575
Tyr Ser Ile Val Gly Lys Tyr Leu Glu His Ala Arg Ile Tyr Tyr Phe
            580                 585                 590
Lys His Glu Asn Ile Tyr Phe Ser Ser Ala Asp Leu Met Pro Arg Asn
        595                 600                 605
Leu Glu Arg Arg Val Glu Leu Leu Ile Pro Ala Thr Asn Pro Lys Ile
    610                 615                 620
```

-continued

```
Ala His Lys Leu Leu His Ile Leu Glu Ile Gln Leu Lys Asp Thr Leu
625                 630                 635                 640

Lys Arg Tyr Glu Leu Asn Ser Lys Gly Arg Tyr Ile Lys Val Ser Asn
            645                 650                 655

Pro Asn Asp Pro Leu Asn Ser Gln Asp Tyr Phe Glu Lys Gln Ala Leu
        660                 665                 670

Lys Thr Phe
        675

<210> SEQ ID NO 13
<211> LENGTH: 688
<212> TYPE: PRT
<213> ORGANISM: Escherichia coli E24377A

<400> SEQUENCE: 13

Met Gly Gln Glu Lys Leu Tyr Ile Glu Lys Glu Leu Ser Trp Leu Ser
1               5                   10                  15

Phe Asn Glu Arg Val Leu Gln Glu Ala Ala Asp Lys Ser Asn Pro Leu
            20                  25                  30

Ile Glu Arg Met Arg Phe Leu Gly Ile Tyr Ser Asn Asn Leu Asp Glu
        35                  40                  45

Phe Tyr Lys Val Arg Phe Ala Glu Leu Lys Arg Arg Ile Ile Ile Ser
    50                  55                  60

Glu Glu Gln Gly Ser Asn Ser His Ser Arg His Leu Leu Gly Lys Ile
65                  70                  75                  80

Gln Ser Arg Val Leu Lys Ala Asp Gln Glu Phe Asp Gly Leu Tyr Asn
                85                  90                  95

Glu Leu Leu Leu Glu Met Ala Arg Asn Gln Ile Phe Leu Ile Asn Glu
            100                 105                 110

Arg Gln Leu Ser Val Asn Gln Asn Trp Leu Arg His Tyr Phe Lys
        115                 120                 125

Gln Tyr Leu Arg Gln His Ile Thr Pro Ile Leu Ile Asn Pro Asp Thr
    130                 135                 140

Asp Leu Val Gln Phe Leu Lys Asp Asp Tyr Thr Tyr Leu Ala Val Glu
145                 150                 155                 160

Ile Ile Arg Gly Asp Thr Ile Arg Tyr Ala Leu Leu Glu Ile Pro Ser
                165                 170                 175

Asp Lys Val Pro Arg Phe Val Asn Leu Pro Pro Glu Ala Pro Arg Arg
            180                 185                 190

Arg Lys Pro Met Ile Leu Leu Asp Asn Ile Leu Arg Tyr Cys Leu Asp
        195                 200                 205

Asp Ile Phe Lys Gly Phe Phe Asp Tyr Asp Ala Leu Asn Ala Tyr Ser
    210                 215                 220

Met Lys Met Thr Arg Asp Ala Glu Tyr Asp Leu Val His Glu Met Glu
225                 230                 235                 240

Ala Ser Leu Met Glu Leu Met Ser Ser Leu Lys Gln Arg Leu Thr
                245                 250                 255

Ala Glu Pro Val Arg Phe Val Tyr Gln Arg Asp Met Pro Asn Ala Leu
            260                 265                 270

Val Glu Val Leu Arg Glu Lys Leu Thr Ile Ser Arg Tyr Asp Ser Ile
        275                 280                 285

Val Pro Gly Gly Arg Tyr His Asn Phe Lys Asp Phe Ile Asn Phe Pro
    290                 295                 300

Asn Val Gly Lys Ala Asn Leu Val Asn Lys Pro Leu Pro Arg Leu Arg
305                 310                 315                 320
```

His Ile Trp Phe Asp Lys Ala Gln Phe Arg Asn Gly Phe Asp Ala Ile
                325                 330                 335

Arg Glu Arg Asp Val Leu Leu Tyr Tyr Pro Tyr His Thr Phe Glu His
            340                 345                 350

Val Leu Glu Leu Leu Arg Gln Ala Ser Phe Asp Pro Ser Val Leu Ala
        355                 360                 365

Ile Lys Ile Asn Ile Tyr Arg Val Ala Lys Asp Ser Arg Ile Ile Asp
    370                 375                 380

Ser Met Ile His Ala Ala His Asn Gly Lys Lys Val Thr Val Val Val
385                 390                 395                 400

Glu Leu Gln Ala Arg Phe Asp Glu Glu Ala Asn Ile His Trp Ala Lys
                405                 410                 415

Arg Leu Thr Glu Ala Gly Val His Val Ile Phe Ser Ala Pro Gly Leu
            420                 425                 430

Lys Ile His Ala Lys Leu Phe Leu Ile Ser Arg Lys Glu Asn Gly Glu
        435                 440                 445

Val Val Arg Tyr Ala His Ile Gly Thr Gly Asn Phe Asn Glu Lys Thr
    450                 455                 460

Ala Arg Leu Tyr Thr Asp Tyr Ser Leu Leu Thr Ala Asp Ala Arg Ile
465                 470                 475                 480

Thr Asn Glu Val Arg Arg Val Phe Asn Phe Ile Glu Asn Pro Tyr Arg
                485                 490                 495

Pro Val Thr Phe Asp Tyr Leu Met Val Ser Pro Gln Asn Ser Arg Arg
            500                 505                 510

Leu Leu Tyr Glu Met Val Asp Arg Glu Ile Ala Asn Ala Gln Gln Gly
        515                 520                 525

Leu Pro Ser Gly Ile Thr Leu Lys Leu Asn Asn Leu Val Asp Lys Gly
    530                 535                 540

Leu Val Asp Arg Leu Tyr Ala Ala Ser Ser Gly Val Pro Val Asn
545                 550                 555                 560

Leu Leu Val Arg Gly Met Cys Ser Leu Ile Pro Asn Leu Glu Gly Ile
                565                 570                 575

Ser Asp Asn Ile Arg Ala Ile Ser Ile Val Asp Arg Tyr Leu Glu His
            580                 585                 590

Asp Arg Val Tyr Ile Phe Glu Asn Gly Gly Asp Lys Lys Val Tyr Leu
        595                 600                 605

Ser Ser Ala Asp Trp Met Thr Arg Asn Ile Asp Tyr Arg Ile Glu Val
    610                 615                 620

Ala Thr Pro Leu Leu Asp Pro Arg Leu Lys Gln Arg Val Leu Asp Ile
625                 630                 635                 640

Ile Asp Ile Leu Phe Ser Asp Thr Val Lys Ala Arg Tyr Ile Asp Lys
                645                 650                 655

Glu Leu Ser Asn Arg Tyr Val Pro Arg Gly Asn Arg Lys Val Arg
            660                 665                 670

Ala Gln Leu Ala Ile Tyr Asp Tyr Ile Lys Ser Leu Glu Gln Pro Glu
        675                 680                 685

<210> SEQ ID NO 14
<211> LENGTH: 701
<212> TYPE: PRT
<213> ORGANISM: Vibrio cholerae

<400> SEQUENCE: 14

Met Ser Ala Asp Lys Leu Tyr Ile Asp Lys Glu Leu Ser Trp Leu Ser

-continued

```
1               5                    10                   15

Phe Asn Glu Arg Val Leu Gln Glu Ala Ala Asp Lys Thr Val Pro Leu
                    20                  25                  30

Ile Glu Arg Ile Arg Phe Leu Gly Ile Phe Ser Asn Asn Leu Asp Glu
                    35                  40                  45

Phe Tyr Lys Val Arg Phe Ala Asp Val Lys Arg Gln Ile Leu Ile Asn
                    50                  55                  60

Arg Glu Arg Gly Gly Asn Asp Ile Ser Lys His Leu Leu Ser Arg Met
    65                  70                  75                  80

Gln Ser Lys Ala Leu Lys Leu Asn Gln Asp Phe Asp Asn Leu Tyr Asn
                    85                  90                  95

Glu Leu Ile Leu Glu Met Ala Arg Arg Ile Phe Leu Val Asn Glu
                    100                 105                 110

Thr Gln Leu Asp Glu Ile Gln Leu Lys Trp Val Lys Lys Tyr Phe His
                    115                 120                 125

Lys Val Met Leu Pro His Val Thr Pro Ile Met Leu Arg Asp Asp Ile
                    130                 135                 140

Asp Val Met Gln Phe Leu Lys Asp Glu Tyr Ala Tyr Ile Ala Val Glu
    145                 150                 155                 160

Met Arg Ser Gly Asp Glu Phe Lys Tyr Ala Leu Ile Glu Ile Pro Thr
                    165                 170                 175

Asp Gln Leu Pro Arg Phe Val Met Leu Pro Glu Gln Lys Gly Lys Arg
                    180                 185                 190

Arg Lys Thr Ile Ile Leu Leu Asp Asn Ile Ile Arg Leu Cys Leu Asp
                    195                 200                 205

Glu Ile Phe Arg Gly Phe Tyr Asp Tyr Asp Thr Leu Asn Gly Tyr Ala
    210                 215                 220

Met Lys Met Thr Arg Asp Ala Glu Tyr Asp Leu Arg His Glu Val Glu
    225                 230                 235                 240

Tyr Ser Leu Leu Glu Gln Met Ser Glu Gly Leu Ser Gln Arg Leu Thr
                    245                 250                 255

Ala Leu Pro Val Arg Phe Val Tyr Glu Arg Glu Met Pro Glu Ala Met
                    260                 265                 270

Leu Lys Phe Leu Cys Tyr Lys Leu Lys Ile Ser His Tyr Asp Ser Leu
                    275                 280                 285

Ile Pro Gly Gly Arg Tyr His Asn Phe Lys Asp Phe Ile Ser Phe Pro
                    290                 295                 300

Asn Val Gly Arg Asp Tyr Leu Glu Asn Lys Pro Leu Pro Pro Met Thr
    305                 310                 315                 320

Cys Ala Asp Phe Glu Gly Tyr Ala Asn Ala Phe Asp Ala Ile Arg Ala
                    325                 330                 335

Gln Asp Ile Leu His Tyr Pro Tyr His Ser Phe Glu His Met Thr
                    340                 345                 350

Glu Leu Val Arg Gln Ala Ser Phe Asp Pro Lys Val Val Ser Ile Lys
                    355                 360                 365

Ile Asn Ile Tyr Arg Val Ala Lys Asp Ser Lys Leu Met Asn Ser Leu
                    370                 375                 380

Val Asp Ala Val His Asn Gly Lys Arg Val Val Val Val Glu Leu
    385                 390                 395                 400

Gln Ala Arg Phe Asp Glu Glu Ala Asn Ile Glu Trp Ser Arg Ile Leu
                    405                 410                 415

Thr Asp Ala Gly Val His Val Ile Phe Gly Val Pro Gly Met Lys Ile
                    420                 425                 430
```

His Ala Lys Leu Leu Ile Thr Arg Lys Glu Gly Asp Glu Phe Val
            435                 440                 445

Arg Tyr Ala His Ile Gly Thr Gly Asn Phe His Glu Arg Thr Ala Arg
    450                 455                 460

Ile Tyr Thr Asp Phe Ala Leu Leu Thr Ala Asn Gln Glu Leu Ala Ala
465                 470                 475                 480

Glu Val Arg Ala Val Phe Gly Tyr Ile Glu Asn Pro Phe Arg Pro Val
                485                 490                 495

Lys Phe Asn His Leu Ile Val Ser Pro Arg Asn Ser Arg Thr Gln Ile
            500                 505                 510

Tyr Arg Leu Leu Asp Ser Glu Ile Ala Asn Ala Lys Ala Gly Lys Lys
        515                 520                 525

Ala Ala Ile Thr Leu Lys Val Asn Asn Leu Val Asp Lys Gly Leu Ile
    530                 535                 540

Asn Lys Leu Tyr Gly Ala Ser Ala Ala Gly Val Lys Ile Arg Met Ile
545                 550                 555                 560

Ile Arg Gly Met Cys Ser Leu Val Pro Gly Val Glu Gly Val Ser Asp
                565                 570                 575

Asn Ile Glu Ile Ile Ser Ile Ile Asp Arg Phe Leu Glu His Pro Arg
            580                 585                 590

Val Leu Val Val His Asn Asp Gly Asn Pro Gln Val Phe Ile Ser Ser
        595                 600                 605

Ala Asp Trp Met Glu Arg Asn Ile Asp His Arg Ile Glu Val Met Ala
    610                 615                 620

Pro Ile Arg Asp Glu Arg Leu Lys Gln Arg Ile Asp Ile Leu Asn
625                 630                 635                 640

Ile Gln Phe Ile Asp Thr Val Lys Ala Arg Ile Asp Lys Glu Met
            645                 650                 655

Ser Asn Gln Tyr Val Glu Arg Gly Asn Arg Lys Val Arg Ser Gln
                660                 665                 670

Ile Ala Ile Tyr Asp Tyr Leu Lys Asn Val Glu Lys Gln Thr Arg Lys
        675                 680                 685

Ala Lys Gly Gln Gln Glu Thr Asn Asp Asn Ser Ser Gln
    690                 695                 700

<210> SEQ ID NO 15
<211> LENGTH: 736
<212> TYPE: PRT
<213> ORGANISM: Pseudomonas aeruginosa PAO1

<400> SEQUENCE: 15

Met Asn Thr Gln Gln Gly Leu Asp Glu Ile Glu Arg Ile Ala Ala Asp
1               5                   10                  15

Glu Thr Val Val Ala Asn Val Glu Ser Glu Ala Glu Val Lys Met Ala
                20                  25                  30

Glu Thr Ile Pro Val Glu Thr Pro Pro Ala Val Val Pro Ser Val Asp
            35                  40                  45

Asp Ser Ser Leu Tyr Ile His Arg Glu Leu Ser Gln Leu Gln Phe Asn
    50                  55                  60

Ile Arg Val Leu Glu Gln Ala Leu Asp Glu Ser Tyr Pro Leu Leu Glu
65                  70                  75                  80

Arg Leu Lys Phe Leu Leu Ile Phe Ser Ser Asn Leu Asp Glu Phe Phe
                85                  90                  95

Glu Ile Arg Ile Ala Gly Leu Lys Lys Gln Ile Thr Phe Ala Arg Glu

```
            100                 105                 110
Gln Ala Gly Ala Asp Gly Leu Leu Pro His Gln Ala Leu Ala Arg Ile
        115                 120                 125

Ser Glu Leu Val His Glu Gln Val Ser Arg Gln Tyr Arg Ile Leu Asn
        130                 135                 140

Glu Thr Leu Leu Pro Glu Leu Ala Lys His Gln Ile Arg Phe Ile Arg
145                 150                 155                 160

Arg Arg His Trp Thr Leu Lys Ile Lys Thr Trp Val Arg Arg Phe Phe
                    165                 170                 175

Arg Asp Glu Ile Ala Pro Ile Ile Thr Pro Ile Gly Leu Asp Pro Thr
                    180                 185                 190

His Pro Phe Pro Leu Leu Val Asn Lys Ser Leu Asn Phe Ile Val Glu
            195                 200                 205

Leu Glu Gly Met Asp Ala Phe Gly Arg Asp Ser Gly Leu Ala Ile Ile
        210                 215                 220

Pro Ala Pro Arg Leu Leu Pro Arg Ile Ile Arg Leu Pro Glu Asp Val
225                 230                 235                 240

Gly Gly Glu Gly Asp Asn Tyr Val Phe Leu Ser Ser Met Ile His Ala
                    245                 250                 255

His Ala Asp Asp Leu Phe Pro Gly Met Lys Val Lys Gly Cys Tyr Gln
                    260                 265                 270

Phe Arg Leu Thr Arg Asn Ala Asp Leu Ser Val Asp Thr Glu Asp Val
            275                 280                 285

Glu Asp Leu Ala Arg Ala Leu Arg Gly Glu Leu Phe Ser Arg Arg Tyr
        290                 295                 300

Gly Asp Ala Val Arg Leu Glu Val Val Asp Thr Cys Pro Gln Asn Leu
305                 310                 315                 320

Thr Asn Tyr Leu Leu Lys Gln Phe Gly Leu Ser Glu Ser Glu Leu Tyr
                    325                 330                 335

Lys Val Ser Gly Pro Val Asn Leu Thr Arg Leu Phe Ser Val Thr Gly
                    340                 345                 350

Leu Glu Ser His Pro Glu Leu Gln Tyr Pro Pro Phe Thr Pro Ala Ile
            355                 360                 365

Pro Arg Leu Leu Gln Lys Lys Glu Asn Leu Phe Asn Val Leu Ser Lys
        370                 375                 380

Leu Asp Val Leu Met His Pro Phe Glu Ser Phe Thr Pro Val Ile
385                 390                 395                 400

Asp Leu Leu Arg Gln Ala Ala Lys Asp Pro Asn Val Leu Ala Ile Lys
                    405                 410                 415

Gln Thr Leu Tyr Arg Ser Gly Ala Asn Ser Glu Ile Val Asp Ala Leu
                    420                 425                 430

Val Glu Ala Ala Arg Asn Gly Lys Glu Val Thr Ala Val Ile Glu Leu
            435                 440                 445

Arg Ala Arg Phe Asp Glu Glu Ser Asn Leu Gln Leu Ala Ser Arg Leu
        450                 455                 460

Gln Gln Ala Gly Ala Val Val Ile Tyr Gly Val Val Gly Phe Lys Thr
465                 470                 475                 480

His Ala Lys Met Met Leu Ile Leu Arg Arg Glu Asp Gly Glu Leu Arg
                    485                 490                 495

Arg Tyr Ala His Leu Gly Thr Gly Asn Tyr His Ala Gly Asn Ala Arg
                    500                 505                 510

Leu Tyr Thr Asp Tyr Ser Leu Leu Thr Ala Asp Val Ala Leu Cys Glu
            515                 520                 525
```

```
Asp Leu His Lys Leu Phe Asn Gln Leu Ile Gly Met Gly Lys Thr Leu
        530                 535                 540

Arg Met Lys Lys Leu Leu His Ala Pro Phe Thr Leu Lys Lys Asn Leu
545                 550                 555                 560

Leu Glu Met Ile Asn Arg Glu Ala Ala Gln Ala Ala Leu Gly Gln Pro
                565                 570                 575

Ala His Ile Met Ala Lys Val Asn Ser Leu Thr Asp Pro Lys Val Ile
                580                 585                 590

Arg Ala Leu Tyr Lys Ala Ser Gln Ala Gly Val Arg Ile Asp Leu Val
                595                 600                 605

Val Arg Gly Met Cys Cys Leu Arg Pro Gly Ile Pro Gly Val Ser His
610                 615                 620

Asn Ile His Val Arg Ser Ile Ile Gly Arg Phe Leu Glu His Ser Arg
625                 630                 635                 640

Ile Tyr Tyr Phe Leu Asn Gly Gly Asp Glu Lys Leu Tyr Leu Ser Ser
                645                 650                 655

Ala Asp Trp Met Glu Arg Asn Leu Asp Met Arg Val Glu Thr Cys Phe
                660                 665                 670

Pro Val Glu Gly Lys Lys Leu Val Gln Arg Val Lys Lys Glu Leu Glu
                675                 680                 685

Thr Tyr Leu Thr Asp Asn Thr Gln Ala Trp Val Leu Gln Ala Asp Gly
                690                 695                 700

Ser Tyr Gln Arg Leu Ser Pro Thr Gly Asn Gln Asn Pro Arg Asn Thr
705                 710                 715                 720

Gln Ala Thr Leu Leu Glu Lys Leu Ala Ala Pro Val Leu Thr Ala Arg
                725                 730                 735

<210> SEQ ID NO 16
<211> LENGTH: 702
<212> TYPE: PRT
<213> ORGANISM: Bacillus anthracis str. Ames

<400> SEQUENCE: 16

Met Glu Leu Ser Lys Gly Asn Ile Val Asn Leu Asn Asp Thr Ala Tyr
1               5                   10                  15

Tyr Asn Asn Arg Glu Leu Ser Trp Leu Ala Phe Asn Glu Arg Val Leu
                20                  25                  30

Gln Glu Ala Gln Asp Glu Thr Asn Pro Leu Leu Glu Arg Leu Lys Phe
                35                  40                  45

Ile Ser Ile Phe Ser Ser Asn Leu Asp Glu Phe Met Val Arg Val
        50                  55                  60

Ala Gly Leu Lys Asp Gln Val Ser Ala Gly Phe Asn Gln Pro Glu Asn
65                  70                  75                  80

Lys Ala Gly Leu Thr Pro Lys Lys Gln Leu Asn Lys Ile Ala Ile Lys
                85                  90                  95

Ala His Glu Leu Met Thr Val Gln Tyr Gly Thr Phe Lys Asn Tyr Val
                100                 105                 110

Leu Pro Ala Leu Glu Leu Glu Gly Ile Glu Arg Leu Thr Phe His Asp
                115                 120                 125

Leu Thr Lys Glu Gln Arg Glu Phe Ile Glu Glu Tyr Phe Asp Glu Gln
                130                 135                 140

Ile Phe Pro Val Leu Thr Pro Val Ala Ile Asp Ala Tyr Arg Pro Phe
145                 150                 155                 160

Pro Met Leu Leu Asn Lys Ser Leu Asn Leu Ala Thr Leu Leu Tyr Asp
```

```
            165                 170                 175
Glu Lys Gln Val Glu Glu Asn Arg Thr Lys Leu Gly Ile Val Gln
            180                 185                 190

Val Pro Ser Leu Leu Glu Arg Phe Ile Phe Leu Pro Ser Glu Gly Gln
            195                 200                 205

Lys His Lys Phe Ile Leu Leu Glu Asp Val Ile Ser Ser Phe Thr His
            210                 215                 220

Lys Leu Phe Thr Gly Tyr Lys Val Ser Ser Val Thr Arg Phe Arg Ile
225                 230                 235                 240

Thr Arg Asn Ala Asp Leu Thr Ile His Glu Glu Gly Ala Arg Asp Leu
                245                 250                 255

Leu Lys Val Ile Glu Lys Glu Leu Lys Lys Arg Lys Trp Gly Ala Ala
                260                 265                 270

Val Arg Leu Glu Val Gly Lys Glu His Ile Asp Glu Arg Val Leu Ala
                275                 280                 285

Leu Leu Tyr Glu Val Leu Glu Val Lys Asp Glu Asp Val Tyr Ile Met
                290                 295                 300

Asp Gly Pro Leu Asp Leu Thr Cys Leu Phe Ser Leu Tyr Lys Lys Leu
305                 310                 315                 320

Ala Pro Leu Tyr Glu His Leu Val Tyr Pro Ala Leu Ile Pro Gln Arg
                325                 330                 335

Pro Gln Asp Leu Gly Asp Ala Glu Asp Val Phe Glu Lys Ala Ile Glu
                340                 345                 350

His Asp Ile Leu Leu His His Pro Phe Glu Ser Phe Gln Pro Val Val
                355                 360                 365

Asp Phe Val Arg Asp Ala Ala Asp Pro Asn Val Leu Ala Ile Lys
                370                 375                 380

Gln Thr Leu Tyr Arg Val Ser Gly Asp Ser Pro Ile Ile Gln Ala Leu
385                 390                 395                 400

Lys Ile Ala Ala Glu Lys Gly Lys Gln Val Thr Val Leu Val Glu Leu
                405                 410                 415

Lys Ala Arg Phe Asp Glu Glu Asn Asn Val His Trp Ala Lys Glu Leu
                420                 425                 430

Glu Gln Ala Gly Cys His Val Ile Tyr Gly Val Ser His Leu Lys Thr
                435                 440                 445

His Ser Lys Ile Thr Leu Val Val Arg Arg Lys Asn Gly Lys Ile Glu
                450                 455                 460

Arg Phe Val His Leu Gly Thr Gly Asn Tyr Asn Asp Ala Thr Ala Lys
465                 470                 475                 480

Leu Tyr Thr Asp Phe Gly Tyr Ile Thr Ser Arg Lys Asp Phe Gly Val
                485                 490                 495

Asp Ala Thr Asn Phe Phe Asn Tyr Leu Ser Gly Tyr Thr Thr Lys Pro
                500                 505                 510

His Phe His His Leu Ser Val Ala Pro Phe Asp Ile Arg Glu Gln Phe
                515                 520                 525

Met Asp Leu Ile Asp Glu Glu Ile Arg Tyr His Arg Gln Tyr Gly Asn
                530                 535                 540

Gly Tyr Ile Ile Ala Lys Met Asn Ser Leu Thr Asp Lys Pro Leu Ile
545                 550                 555                 560

Lys Lys Met Tyr Glu Ala Ser Gln Ala Gly Val Lys Val Glu Leu Ile
                565                 570                 575

Val Arg Gly Thr Cys Cys Leu Arg Pro Gly Ile Pro Asn Val Ser Glu
                580                 585                 590
```

```
Asn Ile Arg Val Val Ser Val Val Gly Arg Tyr Leu Glu His Ser Arg
        595                 600                 605

Ile Tyr Tyr Phe His His Asn Gly Glu Glu Lys Ile Tyr Leu Ser Ser
    610                 615                 620

Ala Asp Trp Met Thr Arg Asn Met Glu Lys Arg Val Glu Ile Ser Phe
625                 630                 635                 640

Pro Ile Leu Asp Ile Glu Met Lys Ala Arg Ile Lys Ala Ile Leu Gln
            645                 650                 655

Leu Thr Leu Ala Asp Asn Val Lys Thr Arg Glu Gln Asn Lys Asp Gly
            660                 665                 670

Asp Tyr Tyr Val Ile Asn Ser Gly Ala Glu Glu Ile Asp Ser Gln
        675                 680                 685

Val Lys Leu Phe Lys Met Ala Tyr Gln Asn Thr Asp Ala Glu
    690                 695                 700
```

The invention claimed is:

1. A method of accumulating a polymeric or high molecular weight molecular product within a bacterial microcompartment in bacterial cytoplasm, said method comprising:
   a) providing a recombinant bacteria which is genetically transformed to express a heterologous bacterial microcompartment operon and an enzyme fused to a bacterial microcompartment localisation signal, wherein the enzyme is capable of converting a low molecular weight substrate into a polymeric or high molecular weight product, and wherein microcompartment localization signal peptide is capable of targeting the enzyme to the microcompartment,
   b) incubating the recombinant bacteria with the low-molecular weight substrate, or a precursor of the low molecular weight substrate which is capable of being metabolized to the substrate within the recombinant bacteria, wherein the substrate or precursor is taken up by the bacteria, wherein the substrate enters the microcompartment and the enzyme within the microcompartment converts the substrate to a polymeric or high molecular weight molecular product, and
   wherein the polymeric or high molecular weight molecular product is accumulated within the microcompartment.

2. The method of claim 1, wherein the microcompartment localization signal is defined by SEQ ID NO: 4.

3. The method of claim 1, wherein the microcompartment is a Pdu microcompartment or a microcompartment encoded by three microcompartment operon structural genes.

4. The method of claim 1, wherein the bacteria is selected from *Escherichia coli*, *Lactobacillus*, *Bifidobacteria*, *Pseudomonas*, *Accumilibacter*, *Thermus thermophilus*, *Thermosynechococcus*, *Halomonas* or *Halobacterium* or other salt tolerant species or other bacteria already adapted to function in the system where phosphate uptake is desired.

5. The method of claim 1, wherein the microcompartment prevents endogenous enzymes from coming into contact with the accumulated polymeric or high molecular weight compound.

6. A method of removing inorganic phosphate (Pi) from a system,
   said method comprising:
   a) providing a recombinant bacteria which is genetically transformed to express a heterologous bacterial microcompartment operon and a polyphosphate kinase enzyme fused to a bacterial microcompartment localisation signal, and
   b) incubating the recombinant bacteria with the inorganic phosphate (Pi) precursor substrate in the system, wherein the substrate enters the microcompartment and the enzyme within the microcompartment converts the substrate to a high molecular weight polyphosphate polymer,
   wherein the high molecular weight polyphosphate polymer is accumulated within the microcompartment due to its size.

7. The method of claim 6, wherein the polyphosphate kinase enzyme is PPK1 and is optionally encoded by SEQ ID NO: 3.

8. The method of claim 6, wherein the recombinant bacteria is genetically transformed with:
   a) a plasmid comprising a nucleotide sequence encoding a pdu microcompartment operon, and a nucleotide sequence encoding a PPK1 enzyme fused to a microcompartment localization signal peptide; or
   b) separate plasmids one of which encodes the Pdu microcompartment, and another of which encodes the nucleotide sequence encoding the PPK1 enzyme fused to a microcompartment localization signal peptide.

9. A recombinant bacteria which is genetically transformed to express a heterologous bacterial microcompartment operon and an enzyme fused to a bacterial microcompartment localization signal, wherein the enzyme is capable of converting a low molecular weight substrate into a polymeric or high molecular weight product, wherein the microcompartment has pores that are dimensioned to allow the low molecular weight substrate pass into the microcompartment and prevent the polymeric or high molecular weight molecular products from passing out of the microcompartment.

10. The recombinant bacteria of claim 9, wherein the enzyme is polyphosphate kinase enzyme, and the heterologous bacterial microcompartment operon encodes a Pdu microcompartment or a microcompartment encoded by three microcompartment operon structural genes.

11. The recombinant bacteria of claim 9, wherein the bacteria is selected from *Escherichia coli*, *Lactobacillus*, (*L. reuteri*, *L. acidophilus*, *L. casei*, *L. plantarum*, *L. johnsonii*, *L. rhamnosus*) *Lactococcus lactis*, *Bifidobacteria* (*B. infantis*, *B. breve*, *B. longum*, *Bifidobacterium animalis* ssp. *Lactis*),

*Enterococcus faecalis, E. faecium*), *Streptoccus thermophilus, Pseudomonas, Accumilibacter*, or other *Proteobacteria, Bacteroidetes, Planctomycetales, Firmicutes* or *Actinobacteria* species.

12. The recombinant bacteria of claim 9, wherein the bacterial microcompartment localization signal is defined by SEQ ID NO:4, or a variant thereof capable of targeting the enzyme to the microcompartment.

13. The recombinant bacteria of claim 9, wherein the polyphosphate kinase enzyme is PPK1 and in which the polyphosphate kinase enzyme is optionally encoded by SEQ ID NO: 3.

14. The recombinant bacteria of claim 9, wherein the enzyme is a polyphosphate kinase enzyme PPK1; and the bacterial microcompartment is a Pdu microcompartment or a microcompartment encoded by three microcompartment operon structural genes.

15. A pharmaceutical composition comprising the recombinant bacteria of claim 9 combination with a suitable pharmaceutical excipient.

16. A plasmid comprising a nucleic acid sequence encoding an enzyme fused to a bacterial microcompartment localization signal, said enzyme being capable of converting a low molecular weight substrate into a polymeric or high molecular weight molecular weight product and an empty bacterial microcompartment, wherein the plasmid is capable of expressing within a bacterial host an empty bacterial microcompartment and a fusion protein comprising the enzyme and the microcompartment localisation signal.

17. A kit of parts comprising:
   a first plasmid comprising a nucleic acid sequence encoding: an enzyme fused to a bacterial microcompartment localization signal, said enzyme being capable of converting a low molecular weight substrate into a polymeric or high molecular weight molecular weight product; and
   a second plasmid comprising a nucleic acid sequence encoding a bacterial microcompartment.

* * * * *